US005772855A

United States Patent [19]
Johnson et al.

[11] Patent Number: 5,772,855
[45] Date of Patent: Jun. 30, 1998

[54] PREPARATION OF BIOACTIVE COMPOUNDS BY PLASMA SYNTHESIS

[75] Inventors: Bruce M. Johnson; Walter C. Babcock; James B. West; Dwayne T. Friesen, all of Bend, Oreg.

[73] Assignee: Bend Research, Inc., Bend, Oreg.

[21] Appl. No.: 843,897

[22] Filed: Apr. 17, 1997

[51] Int. Cl.[6] .................................................. G01N 33/53
[52] U.S. Cl. ................... 204/164; 204/157.15; 435/7.1; 435/7.2; 435/7.4; 435/7.8; 435/29
[58] Field of Search ............................. 204/164, 157.15; 435/7.1, 7.2, 7.4, 7.8, 29

[56] References Cited

U.S. PATENT DOCUMENTS

| | | | |
|---|---|---|---|
| 5,143,854 | 9/1992 | Pirrung et al. | 436/518 |
| 5,556,752 | 9/1996 | Lockhart et al. | 435/6 |

FOREIGN PATENT DOCUMENTS

| | | |
|---|---|---|
| 0 565 275 | 10/1993 | European Pat. Off. |
| WO95/18781 | 7/1995 | WIPO . |

OTHER PUBLICATIONS

Hamblyn et al., "Us of Radio–Frequency Plasma in Chemical Synthesis," 17 *Adv. Inorg. Radiochem* 89 (1975) no month available.

Parsons, "The use of plasmas in chemical synthesis," *J. Inst. Fuel* 524 (Dec. 1970).

Simiorescu et al., "The Use of Plasma–Chemistry in the Field of Synthesis and Modification of the Natural Macromolecular compounds," 14 *Cellulose Chem. Technol.* 285 (1980) no month available.

So et al., "Cyanation of Aromatic Compunds in a Gaseous Plasma," 103 *J.A.C.S.* 4204 (1981) no month available.

Stokes et al., "Use of a Radio Frequency Plasma Jet in Chemical Synthesis," 11 *A.I.Ch.E. Journal* 376 (Mar., 1965).

Suhr, "Organic Syntheses in Plasma of Glow Discharges and Their Preparative Application," 11 *Angew. Chem. Interat. Edit.* 781 (1972) no month available.

*Primary Examiner*—Kathryn L. Gorgos
*Assistant Examiner*—Kishor Mayekar
*Attorney, Agent, or Firm*—Chernoff, Vilhauer, McClung & Stenzel, LLP

[57] ABSTRACT

Large numbers of bioactive compounds of great chemical diversity may be rapidly prepared by subjecting organic compound mixtures to a plasma discharge, followed by screening for specific bioactivity.

18 Claims, 13 Drawing Sheets

PREPARATION OF BIOACTIVE COMPOUNDS BY PLASMA SYNTHESIS

BACKGROUND OF THE INVENTION

Modern drug discovery has been revolutionized by the development of high-throughput screening techniques. The ability to clone receptors, combined with modern automation techniques, means that now thousands of compounds can be screened for receptor binding and, by extension, pharmaceutical activity, in the time previously required to screen only a few. Hodgson, 10 *Biotech.* 973 (1992). Because of this screening capacity, new compound generation is now often the rate-limiting step in drug discovery. Dewitt, 1 *Pharm. News* 11 (1994). In addition, the statistics of this screening approach to drug discovery requires the testing of many thousands of compounds in order to discover one highly active new compound. The traditional sources of compounds for screening, such as natural products or the products of rational drug design, cannot furnish the numbers of compounds needed to meet this demand, while combinatorial synthesis produces large numbers of compounds but they have insufficient diversity of structures. The present invention is directed at the development of a new method to synthesize and screen large numbers of structurally diverse compounds.

There are two principal ways in which candidate compounds are currently provided for drug screening: isolation from natural products, and chemical synthesis. Natural products, such as plant extracts, provide a great amount of structural diversity. However, this approach typically requires laborious sample collection and preparation, followed by difficulties in identification, isolation, and production of compounds determined to be active via screening. Consequently, this approach is typically too slow to meet the capacity offered by high-throughput screening. Traditional chemical synthesis is also slow, and new technologies—primarily combinatorial approaches to stepwise synthesis—are being developed to rapidly generate collections of molecules for drug discovery. Dewitt, Ibid. Such combinatorial approaches can provide sufficient quantities of compounds quickly enough for high-throughput screening, but the structural diversity is restricted due to the limited number of starting materials and synthetic reactions for combining starting materials.

Plasma glow discharges have been used to prepare specific compounds from vaporized organic reactants. See, for example, Cvetanovic, 1 *Adv. Photochem.* 115 (1963) wherein the production of an aldhyde, two epoxides and two ketones from a mixture of 2-pentene and oxygen was reported. See also, Suhr, 11 *Angew. Chem. Int. Ed. Engl.* 781 (1972), which discloses the limited production of several cyclic compounds from acetylene; however, unless the reaction is rapidly quenched, the primary products are polymers. *Ibid.* The primary focus of prior attempts to synthesize new products by exposure of one or more reactants to a glow discharge has been to maximize conversion and yield of a single desired product which, due to the inherent difficulty in controlling plasma discharge reactions, has been largely unsuccessful. The present invention is based upon the recognition that such inherent uncontrollability can be used to advantage in preparing a multitude of organic compounds containing diverse chemical structures and functional groups, and that the resultant product mix, when coupled with bioactivity screening, can ultimately lead to the production of significant numbers of useful compounds.

SUMMARY OF THE INVENTION

The present invention comprises a novel process for synthesizing and identifying compounds with desirable bioactivity. Such compounds are useful in many areas of science and industry, such as the areas of drug discovery, toxicity testing, development of animal and plant growth hormones, and pesticide and herbicide development. The present invention utilizes a new, fast, low-cost method for the generation of mixtures of large numbers of unique compounds in the laboratory: plasma synthesis. As with natural sources of extracts, plasma synthesis promises to provide compounds with an extremely wide variety of structures for testing, but does not require laborious biological-sample collection and preparation. Sample generation may be conducted in the laboratory using small scale apparatus and a wide range of commonly available starting materials. Production of larger samples of promising bioactive materials will therefore be greatly simplified. Because of the high-energy synthesis procedures used, highly diverse structures can be generated from simple starting materials, yet reaction conditions can be adjusted such that the number of products, their molecular weights, and their chemical properties can be controlled. In addition, the number of unique compounds that can be generated using low-cost apparatus rivals that of the best combinatorial techniques.

The process envisioned for synthesis of compound mixtures is not strictly limited to plasma synthesis, but encompasses the interaction of a starting material with any high-energy source that can induce reaction of the starting material to produce a diverse set of products.

For example, a plasma itself is a complex environment. Starting materials exposed to a plasma can interact with ionizing radiation (e.g., radiation of sufficient energy to induce ionization of molecules such as ultraviolet (UV) or higher energy light), non-ionizing radiation (e.g., lower energy radiation that generally does not induce ionization such as near UV or visible light) and electric fields (e.g., those from radio frequency, audio frequency, alternating current or direct current), all of which may be present in the plasma. Any and all of these can impart sufficient energy to the starting materials to induce reactions to form new compounds that are different from the starting material.

The process comprises two main steps: (1) the production of organic compound mixtures of unlimited number and diversity by plasma chemical synthesis; and (2) subjecting these compound mixtures to screening tests for a desired biological activity. Once a particular mixture tests positive for desirable activity, the mixture is separated into its individual components by common chemical separation techniques, such as chromatography or extraction, and each component is then retested to determine which ones have activity.

DETAILED DESCRIPTION OF THE PREFERRED EMBODIMENT

Figure 1:
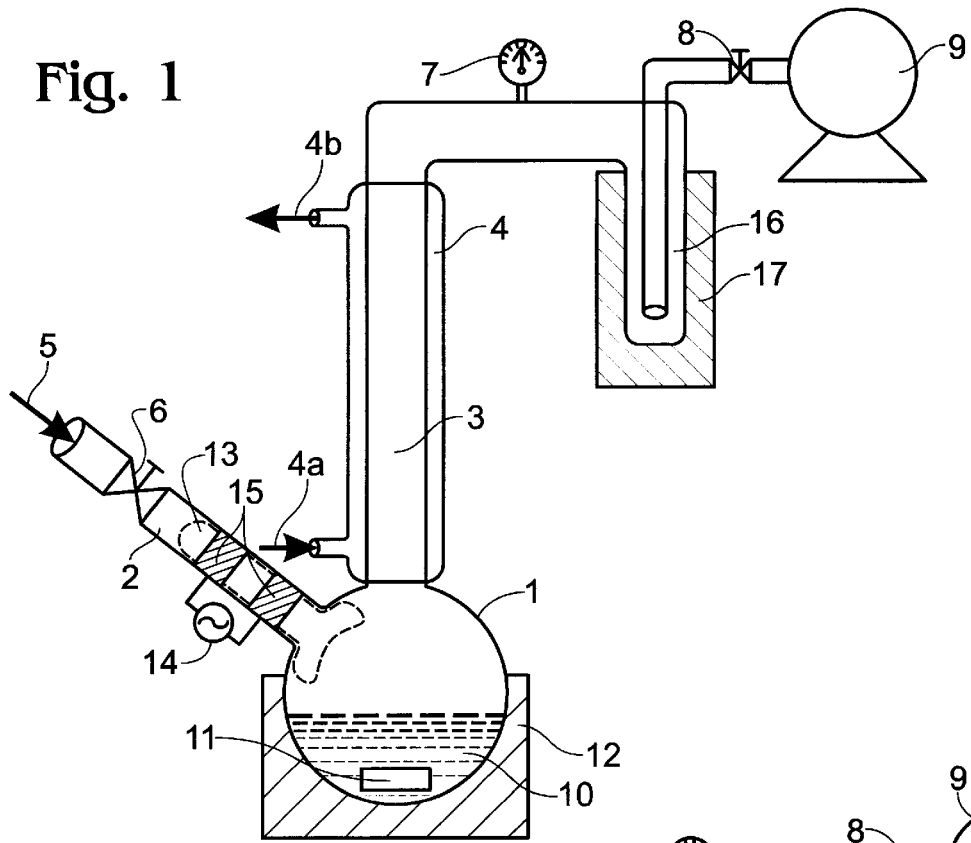
FIGS. 1–8 are schematic drawings of exemplary plasma synthesis reactors that are useful in preparing bioactive compound mixtures.

There are essentially two features of the present invention. In one aspect, the invention comprises a process of preparing mixtures of bioactive organic compounds by interaction of a starting material with a high energy source. In particular, the process comprises plasma chemical synthesis. When conducted in accordance with the methods described in the present invention, a single plasma chemical synthesis run is capable of producing a mixture of 2 to 100 and more diverse and complex organic compounds. Due to the nature of the plasma chemical synthesis process, an unlimited number of unique compound mixtures, comprising all classes of chemical structures and functional groups (e.g., aromatic, halogen, amide, ester, ketone, hydroxyl, ether, mercaptan, cyclic rings containing hetero-atoms, etc.) can be produced.

For the purposes of the present invention, plasma is defined as partially ionized gas, light quanta, radicals, and atomic and molecular species in various electronic excited states. The ionized species consist of positively charged molecules or atoms, and negatively charged electrons, and other ionized species such as negatively charged molecules and atoms and ionized molecular fragments. The recombination of plasma species through collisions with other plasma species, and with neutral molecules, both inside and outside of the plasma zone produces new chemical products and forms the basis of the plasma chemical synthesis process.

Any and all of the high-energy species that make up the plasma can induce reaction of starting material to produce products that make up the resulting mixture of compounds. In addition, simpler processes can be envisioned wherein starting material can interact with energy sources that are not strictly speaking considered plasma (e.g., non-ionizing radiation, ionizing radiators or electric fields), but that have sufficient energy to induce reaction of the starting material and form complex product mixtures in a manner similar to plasma synthesis.

Plasma may be produced by the action of a variety of ionizing agents on molecules and atoms. For example, all molecules and atoms become ionized when heated to temperatures of approximately 10,000° C. or more. However, to prevent decomposition of organic compounds during their synthesis and recovery, the plasma temperature for a practical "cold" plasma organic chemical synthesis process should generally be limited to approximately 350° C. or less. However, in some cases, temperatures may exceed this temperature range as long as the period of time that species are at higher temperatures is very short, for example, on the order of less than 1 second. Cold plasmas are obtainable with an overall temperature of the neutral gaseous products below 350° C. by lowering the gas pressure below 1 atmosphere. Suitable ionizing agents for producing cold plasmas include DC and AC electric discharges; high-energy light sources, such as lasers and electric discharge lamps that produce light in the microwave to x-ray frequency range; and charged particle beams, such as alpha particles produced in controlled nuclear reactions, and electron beams.

A second major aspect of the present invention comprises subjecting the plasma-synthesized organic compound mixtures to bioactivity screening tests. By testing mixtures of compounds, a large number of compounds are rapidly screened for a desired bioactivity. When a particular mixture tests positive for bioactivity, that mixture may then be separated into a number of smaller submixtures, or into fractions containing primarily a single compound. The bioactivity of each compound or submixture may be screened again in order to ultimately identify the particular compound that has the desired bioactivity. Once a fraction that contains primarily a single compound has been shown to be active, its molecular structure can be determined by conventional means such as single or multi-level mass spectroscopy (NMR, IR or UV/visible), and other related methods.

The basic process for preparing mixtures of organic compounds by plasma chemical synthesis comprises the steps of: (1) introducing one or more organic reactants into a plasma synthesis reactor at an appropriate flow rate, and (2) subjecting the reactants to a plasma to form a mixture of product organic compounds.

The plasma may be formed with (1) the entire mixture of reactants, (2) only a portion of the reactants, or (3) an inert gas such as argon. In the case of options (2) and (3), the components that form the plasma are subsequently mixed with any remaining reactants. A key parameter in generating useful mixtures involves controlling the time of contact of the reactants with the plasma. Various methods of obtaining the desired contact time to obtain a high yield of new compounds that have the desired properties are disclosed.

In the present invention, preferred reactants for producing a plasma include any organic or inorganic compound that exhibits a vapor pressure of at least 0.1 torr at a temperature below approximately 350° C. Organic compounds include gases, volatile and semi-volatile liquids, and volatile solids. Exemplary organic compounds include propane, chlorodifluoromethane, acetone, phenol, pyridine, ethanol, benzene, butyl acetate, tetrahydrofuran, ortho-dichlorobenzene, cyclopentanone, allylamine, 5-norbornene-2-methanol, 2-imidazolidone, 9-vinylcarbazole, 3,4-dimethoxyphenethylamine, quinazoline, 2,3-dimethoxybenzylalcohol, resorcinol, olivetol, phenanthrene, pheneanthridine, 1,2,3,4-tetrahydroisoquinoline, 1,2,3,4-tetrahydronapthylamine, methylstearate, ethanolamine, toluene, acetic acid, acetaldehyde, methyl ethyl ketone, and 6-chloro-1-hexanol. In the plasma, these organic compounds ionize and are fragmented to form various excited-state species, such as high-energy electrons, positive and negative ions, radicals, and molecular species in electronically excited states. These excited-state species can recombine directly, and form, through single or multiple collisions, an unlimited variety of new chemical structures, or they can recombine with non excited-state molecules in the gas, liquid, or solid state both within, or outside of, the plasma zone.

Inorganic compounds and elements also include gases and volatile and semi-volatile liquids. Exemplary inorganic reactants include argon, helium, nitrogen, oxygen, water, ammonia, carbon tetrafluoride, hydrogen, carbon monoxide, carbon dioxide and carbon disulfide.

In the case of chemically reactive compounds, such as water and carbon tetrafluoride, excited-state species react directly with each other, or with non excited-state molecules to form new chemical structures. For example, excited-state species resulting from a plasma containing water can introduce hydroxyl groups to starting materials or products of previous reactions to form new chemical structures; carbon tetrafluoride can introduce fluoro or trifluoromethane groups; oxygen can introduce carbonyl, ether, ketone, and various other oxygenated chemical groups; carbon disulfide can introduce thiol, mercapto, and disulfide groups, ammonia can introduce amine groups; nitrogen can introduce nitrile groups; and hydrogen can quench radical species to terminate the synthesis process and can chemically reduce various functional groups, such as carbonyl, alkene, and aromatic groups.

Chemically inert inorganic elements, such as argon and helium, can act as energy transfer reagents for producing new chemical structures. For example, excited-state species formed in argon or helium plasmas can collide with non excited-state organic molecules, either within or outside of the plasma zone, to produce excited-state organic species. The excited-state organic species can then recombine directly, and form through single or multiple collisions, new chemical structures, or they can recombine with non excited-state molecules in the gas, liquid, or solid state both within, or outside of the plasma zone.

Key variables that influence the nature of the compound mixtures produced by the plasma chemical synthesis process include the flow rate of reactants into the plasma zone, the total pressure in the plasma zone, and the amount of energy that is applied to sustain the plasma. The optimum flow of reactants into the plasma synthesis reactor is determined by the optimum residence time of reactants in the plasma zone, and by the plasma operating parameters of pressure and intensity of the ionization source. If the reactants spend too little time in the plasma zone, few collisions occur between reactants and excited-state species, and only a limited amount of products are formed. On the other hand, if the residence time is too long, an excessive number of collisions produces undesirable high molecular weight polymers which, in general, do not exhibit bioactivity. Through experimentation, we have discovered that the optimum range of residence time for reactants in the plasma zone is from 0.001 to 10 seconds, with a preferred range of from 0.01 to 2 seconds. Using this range, the optimum flow of reactants can be calculated by dividing the volume of the plasma zone by the residence time. For example, with a plasma synthesis reactor operated at 1.0 torr pressure and containing a plasma zone 1.5 cm in diameter and 6 cm long, for a desired residence time of 0.05 second the desired flow rate of the reactants would be $\pi r^2 L/tP$, or [6 cm×3.14×(1.5 cm/2)$^2$]/0.05 second ×[1 torr/760 torr (STP)]=0.28 cm$^3$ (STP)/second.

The optimum range of pressure for plasma chemical synthesis is from 0.05 to 10 torr, with a preferred range of from 0.1 to 3 torr. Below 0.05 torr the low collision rate between reactants and excited-state species results in an undesirably low production rate of products. While higher pressure increases the production rate, the plasma temperature also increases. The practical upper limit of pressure is fixed by the plasma temperature and the thermal stability of the complex organic products. For example, through plasma reactor experimentation, it has been discovered that a plasma pressure of approximately 10 torr results in a plasma temperature of approximately 350° C. This temperature corresponds to the thermal stability limit of most organic compounds. However, by modifying the geometry of the reactor and minimizing the residence time of reactants within the plasma zone, one may successfully operate at pressures up to 1 atmosphere, or even higher.

One common method for producing a stable, long-lived plasma is by applying a strong electric field to the reactants in the gas or vapor phase. The strong electric field is typically generated by applying a high frequency voltage source to two ring electrodes that are placed along the plasma reactor, oriented coaxially with respect to the flow of reactants. The ring electrodes can be constructed from strips of electrically conductive material, such as copper, brass, aluminum, or steel, with preferred dimensions of approximately 2 cm wide and 0.1 to 0.5 cm thick, and sufficient length to be bent into a circle approximately 0.5 to 50.0 cm in diameter. The ring electrodes are placed around the interior or exterior of the plasma reactor in the desired region for the plasma zone. When electrode cooling is desired, especially in the case of interior electrodes, the electrodes are constructed from copper, brass, aluminum, or steel tubing from 0.2 to 2 cm diameter and cooling water is passed through the annulus of the electrode. The spacing between the two ring electrodes may range from 1 to 50 cm, with a preferred range of 4 to 20 cm.

The high frequency voltage source consists of an impedance matching network and a high frequency power supply that is capable of supplying from 10 to 5,000 watts of power at a frequency of from 1 kHz to 100 MHz. The preferred frequency range for internal electrodes is from 10 kHz to 50 MHz, and the preferred frequency range for external electrodes is from 10 MHz to 50 MHz. In general, the plasma discharge power must be increased with increasing pressure, increasing reactant flow rate, and with increasing size of the plasma zone. The preferred plasma discharge power is generally the minimum level which gives a stable plasma discharge and produces at least 1% conversion of the reactants to new product compounds within 4 hours reaction time. A preferred range of plasma discharge power for a reactor having a plasma zone volume of approximately 1 liter is from 50 to 500 watts.

In order to take full advantage of the unlimited diversity of chemical structures that may be produced by the plasma chemical synthesis method, a variety of exemplary plasma synthesis reactors have been devised that allow reactions to occur between gaseous, liquid, and solid reactants.

Referring to the drawings, wherein like numerals refer to the same elements, there is shown in FIG. 1 an exemplary reactor for gas, vapor, and liquid reactants. The reactor consists of a glass vacuum flask 1 with reactant inlet 2 and condenser 3. Cooling for condenser 3 is maintained by cooling jacket 4, provided with coolant inlet 4a and outlet 4b; the coolant may be cool air, cool water, or other cooling fluid. Gas or vapor reactants enter the reactor through the reactant inlet opening 5 and flow control valve 6. The desired reactor pressure, which is monitored by pressure gauge 7, is established by opening pressure control valve 8 to vacuum pump 9. Starting material liquid reactant 10 is then brought to a gentle reflux condition by stirring with magnetic stir bar 11 and heating with heating mantle 12. Vapor from the refluxing liquid reactant 10 condenses on the walls of condenser 3 and flows down the walls of the condenser and vacuum flask 1 until it rejoins the pool of liquid reactant 10. Any solid that melts below 350° C., or semi-volatile liquid that exhibits a vapor pressure from 0.1 to 10 torr within the temperature range from 25 to 350° C. is a suitable liquid reactant. A plasma zone 13 (shown by dashed lines) is established by the high frequency voltage source 14 and external ring electrodes 15.

Plasma synthesis products are formed by reaction of excited-state species from the plasma zone and by reaction of excited-state species with reactant vapor from refluxing liquid 10. Products are trapped and removed from further reaction in the plasma zone, and are recovered by dissolving in the refluxing liquid and flowing to the liquid pool in vacuum flask 1. Highly volatile products are collected in cold trap 16, that is supercooled in cooling bath 17; preferably cooling bath 17 is maintained at either about −80° C. by a dry ice slush or at about −200° C. by liquid nitrogen.

Figure 2:
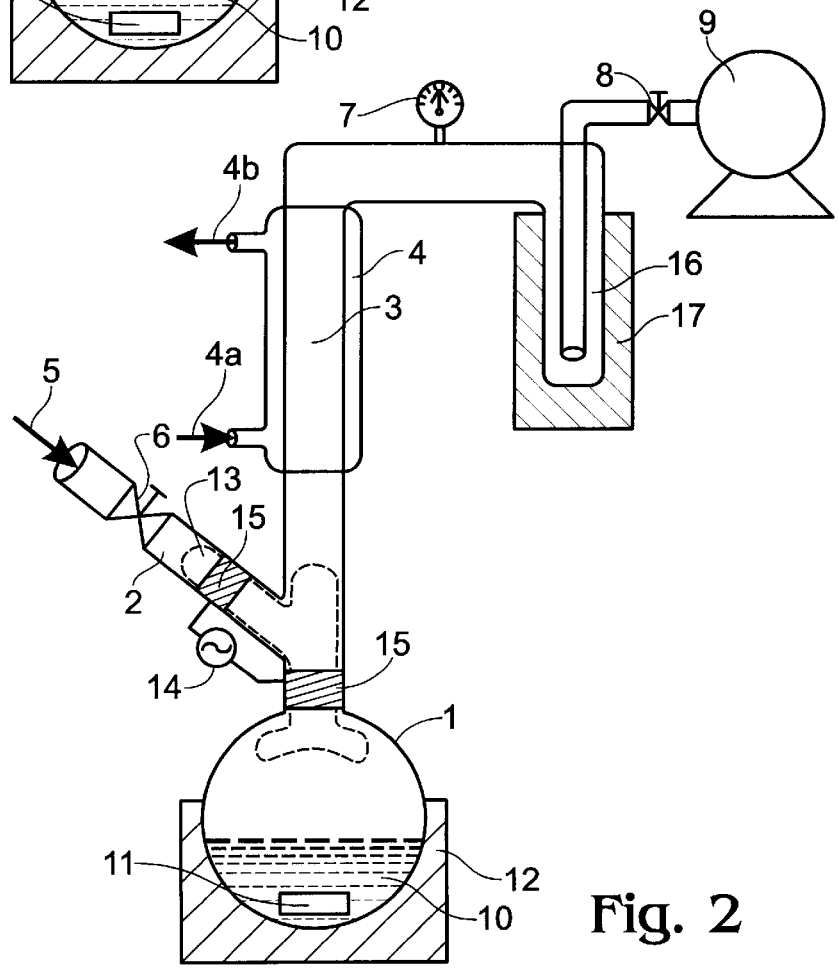

FIG. 2 shows another exemplary reactor for gas, vapor, and liquid reactants. It is similar in design to the reactor shown in FIG. 1 except for the design and placement of glass vacuum flask 1, reactant inlet 2, and external ring electrodes 15. In this reactor configuration, vapor from refluxing liquid reagent 10 must pass through the plasma zone 13 before it condenses on the walls of condenser 3. This results in production of excited-state reactants from liquid reagent 10 as well as from gas or vapor reactants entering the reactor through reactant inlet opening 5. This additional source of excited-state reactants can produce a different range of products compared to use of the same reactants in the reactor shown in FIG. 1.

Figure 3:
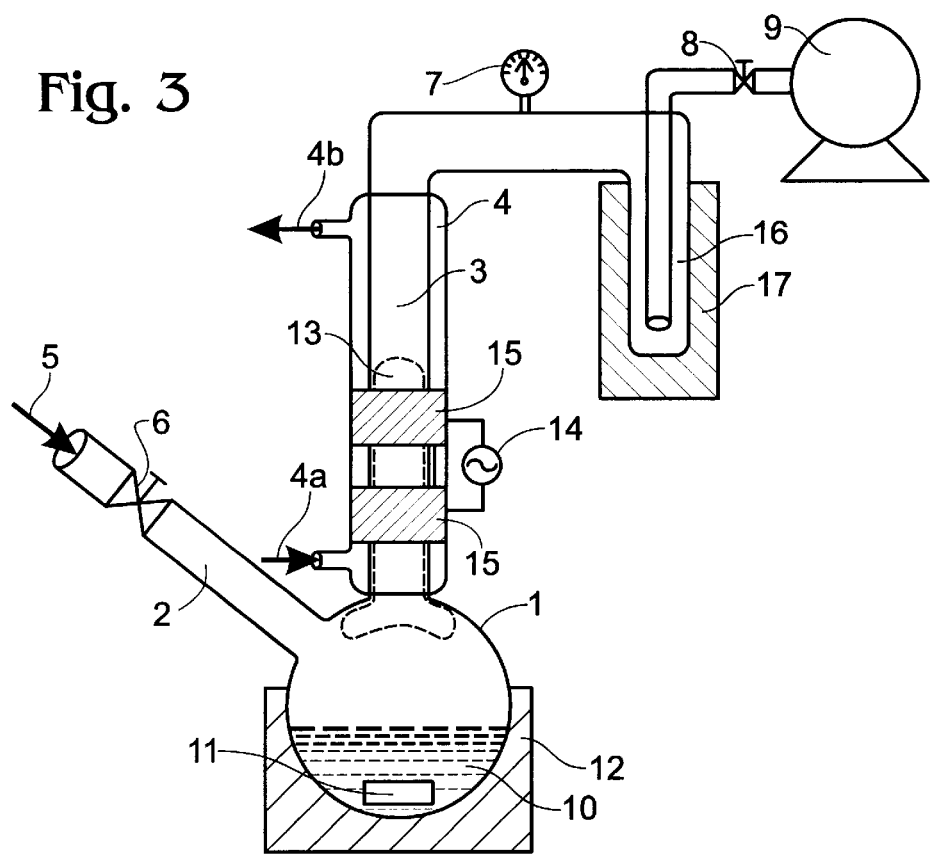

FIG. 3 shows another exemplary reactor for gas, vapor, and liquid reactants. It also is similar in design to the reactor shown in FIG. 1 except for the placement of external ring electrodes 15 around the most active liquid reflux region within condenser 3. In this reactor configuration, a mixture of vapor from refluxing liquid 10 and gas or vapor reactants entering the reactor through reactant inlet opening 5, enter plasma zone 13 to form excited-state species. Plasma synthesis products are formed by reaction between excited-state species in the plasma zone and by reaction between excited-state species and ground-state reactant molecules. Products are trapped and removed from further reaction in the plasma zone, by dissolving in the refluxing liquid film coating the condenser walls and flowing to the liquid pool in vacuum flask 1. Since the plasma zone is located within the most active liquid reflux region of the reactor there is greater contact between excited-state species and vapor from refluxing liquid 10. In addition, the vigorously refluxing liquid improves the trapping and removal of products from the plasma zone. These reactor features can result in production of a still different range of products compared to use of the same reactants in the reactor shown in FIGS. 1 and 2.

Figure 4:
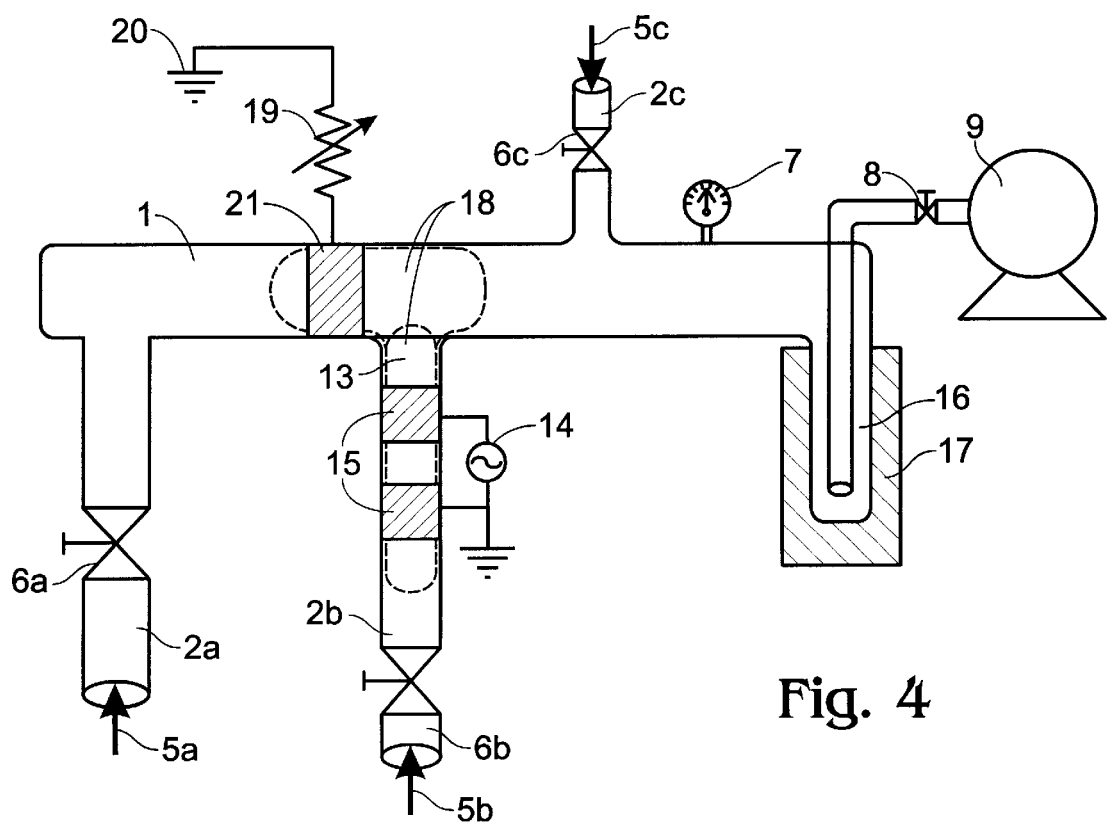

FIG. 4 shows an exemplary reactor useful in preparing compound mixtures from gas and vapor reactants. This reactor requires all reactants to be in the gas or vapor state at a temperature below 350° C. The reactor consists of a heated glass vacuum manifold 1 with multiple reactant inlets 2a, 2b, and 2c. The vacuum manifold and reactant inlets are heated to a temperature of up to 350° C. by a stream of hot air, by application of electric heating coils, or by immersion in a hot oil bath. Gas or vapor reactants enter the reactor through reactant inlet openings 5a, 5b, and 5c and flow control valves 6a, 6b, and 6c. The desired reactor pressure, which is monitored by pressure gauge 7, is established by opening pressure control valve 8 to vacuum pump 9. A plasma zone 13 is established by the high frequency voltage source 14 and external, or internal ring electrodes 15. This reactor provides for a number of useful reactant flow schemes to produce a wide variety of plasma synthesis products.

In the simplest flow scheme, reactants entering the reactor through reactant inlet 2b form excited-state species in the plasma zone and produce products by reaction between excited-state species and by reaction of excited-state species with ground-state reactant molecules. In a second flow scheme, excited-state species formed in the first flow scheme can react with ground-state molecules entering the reactor from both reactant inlets 2a and 2b. An alternative to the second flow scheme is to control and expand the volume of the plasma zone 18 to include formation of excited-state species from reactants entering the reactor through reactant inlet 2a. Control of the volume of the plasma zone is accomplished by applying a variable and controlled impedance 19 to ground 20 for auxiliary internal or external grounded electrode 21.

Yet another series of flow schemes are made possible by combining any of the above flow schemes with introduction of ground state reactant molecules into the reactor through reactant inlet 2c. This last series of flow schemes allows for quenching of residual excited state products by ground state reactant molecules entering the reactor from reactant inlet 2c, down stream from the plasma zone. Products produced in any of the above flow schemes are removed from further reaction in the plasma zone and trapped by convective flow of reactants through the plasma zone to the cold trap 16.

Figure 5:
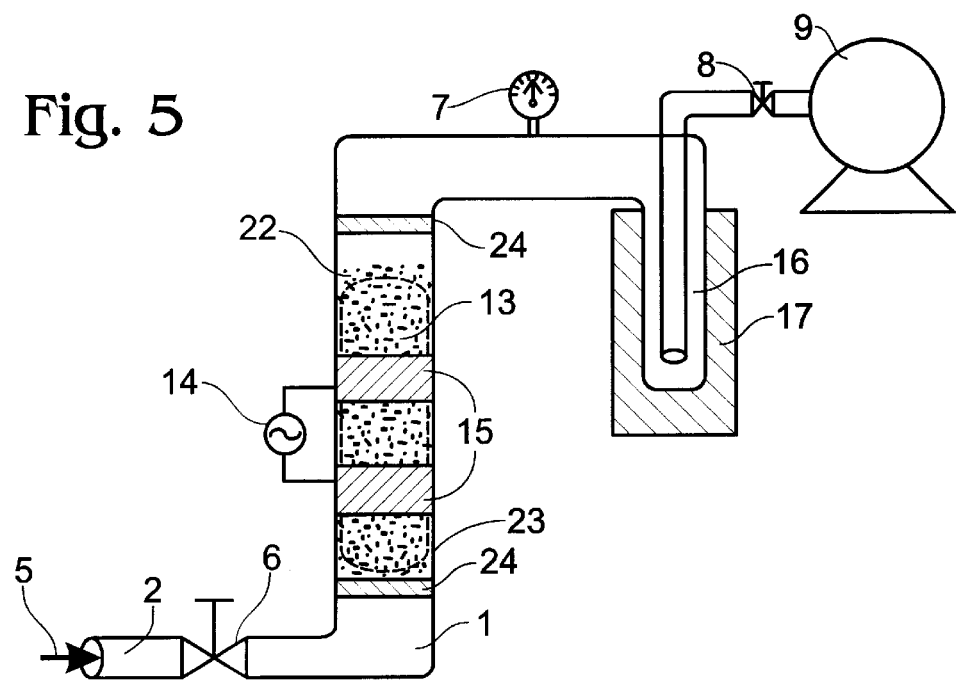

FIG. 5 shows an exemplary reactor useful in preparing compound mixtures from gas, vapor, and solid reactants. This reactor requires one or more of the reactants to be a granular solid at a temperature above 100° C., and requires at least one other reactant in the gas or vapor state at a temperature below the melting point of the solid reactants. The reactor consists of a glass vacuum manifold 1 with reactant inlet 2. Gas or vapor reactants enter the reactor through the reactant inlet opening 5 and flow control valve 6. The flow rate of the gas or vapor reactants is adjusted so that a fluidized bed 22 of solid reactants 23 is maintained within the plasma zone 13 and coalescing filters 24. The desired reactor pressure, which is monitored by pressure gauge 7, is established by opening pressure control valve 8 to vacuum pump 9. A plasma zone 13 is established by the high frequency voltage source 14 and external, or internal ring electrodes 15. Products are produced within the plasma zone by reaction of excited-state species in the gas or vapor phase with the solid reactants at the surface of the fluidized granules. The production of product mixtures from the solid reactants continues as the solid granules are continuously removed from, and reintroduced to, the plasma zone by the action of the fluidized bed. The products are recovered directly from the reactor space between the coalescing filters 24 by turning off the plasma and fluidizing gas or vapor reactants at the optimum reaction time. Highly volatile products are collected in cold trap 16.

Figure 6:
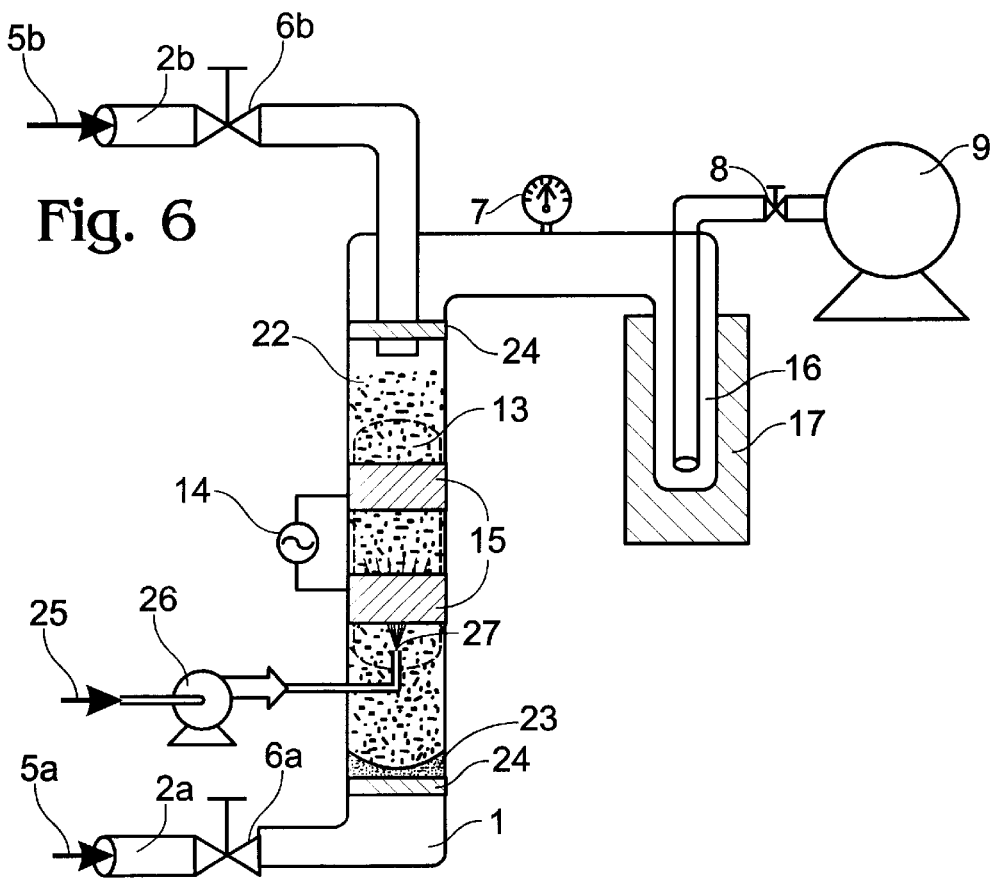

FIG. 6 shows an exemplary reactor that is useful for reacting gas, vapor, volatile liquid, and solid reactants. It is similar in design to the reactor shown in FIG. 5, except for the addition of a second gas or vapor reactant inlet 2b and continuous introduction of solid reactants 23 by spraying a concentrated solution or slurry of the solid reactants into the plasma zone. In this reactor configuration, solid reactants 23 are sprayed into the plasma zone between coalescing filters 24 by introducing a concentrated solution or slurry of the solid reactants 25 into liquid pump 26 and spray head 27. The concentrated solution, or slurry of solid reactants 25 contains at least 10 wt % solid reactants in a solvent that readily volatilizes in the reactor to produce a fine granular fluidized bed of solid reactants 22. Suitable volatile solvents include water, acetone, diethyl ether, toluene, hexane, dichloromethane, and tetrahydrofuran. The fluidized bed is maintained by the spraying and devolitilization process, as well as by introduction of gas or vapor reactants through reactant inlet opening 5a. Excited-state species are therefore formed in the plasma zone 13 from gas or vapor reactants entering the reactor through reactant inlet opening 5a, and from solvent vapor from devolitilization of the concentrated solution or slurry of solid reactants 25. Alternatively, a second source of gas or vapor reactants may be introduced to the plasma zone through reactant inlet opening 5b. This second source of reactants produces additional excited-state species in the plasma zone 13 and the gas or vapor flow may also be used to control movement of fine solid reagent granules back down into the plasma zone.

Figure 7:
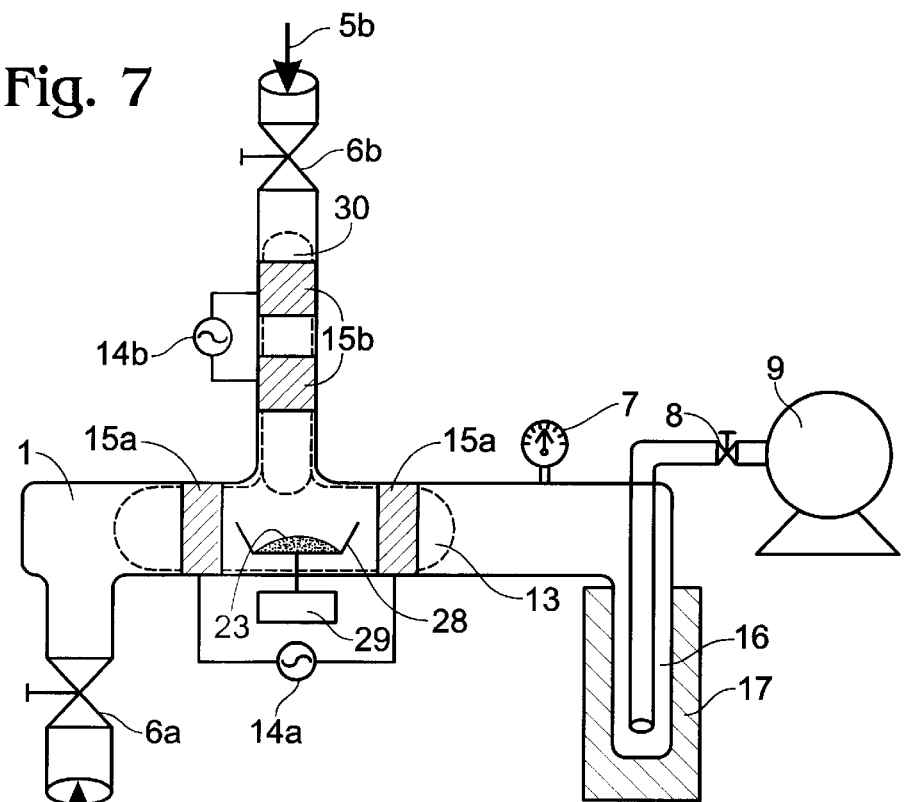

FIG. 7 shows another exemplary reactor that is useful for reacting gas, vapor, and solid reactants. In this reactor configuration, solid reactants 23 are contained in shallow pan 28 within vacuum manifold 1. The shallow pan is located in plasma zone 13, which is maintained by high frequency voltage source 14a and by external or internal ring electrodes 15a. Vibration generator 29 is connected to pan 28 to provide constant mixing of the granular solid reactants and exposure of unreacted granular solid to the plasma. Gas and vapor reactants enter the reactor through the reactant inlet openings 5a and 5b and flow control valves 6a and 6b. Products are produced within the plasma zone by reaction of excited-state species from the gas or vapor phase with the solid reactants at the surface of the tumbling solid reactant granules. Optionally, excited-state species may be formed mainly from gas and vapor reactants entering the reactor at reactant inlet opening 5b, and the solid reactants can be kept out of the plasma zone, by eliminating plasma zone 13 and forming plasma zone 30 through application of high frequency voltage source 14b to internal or external ring electrodes 15b. The products are recovered directly from pan 28 by turning off the plasma at the optimum reaction time.

Figure 8:
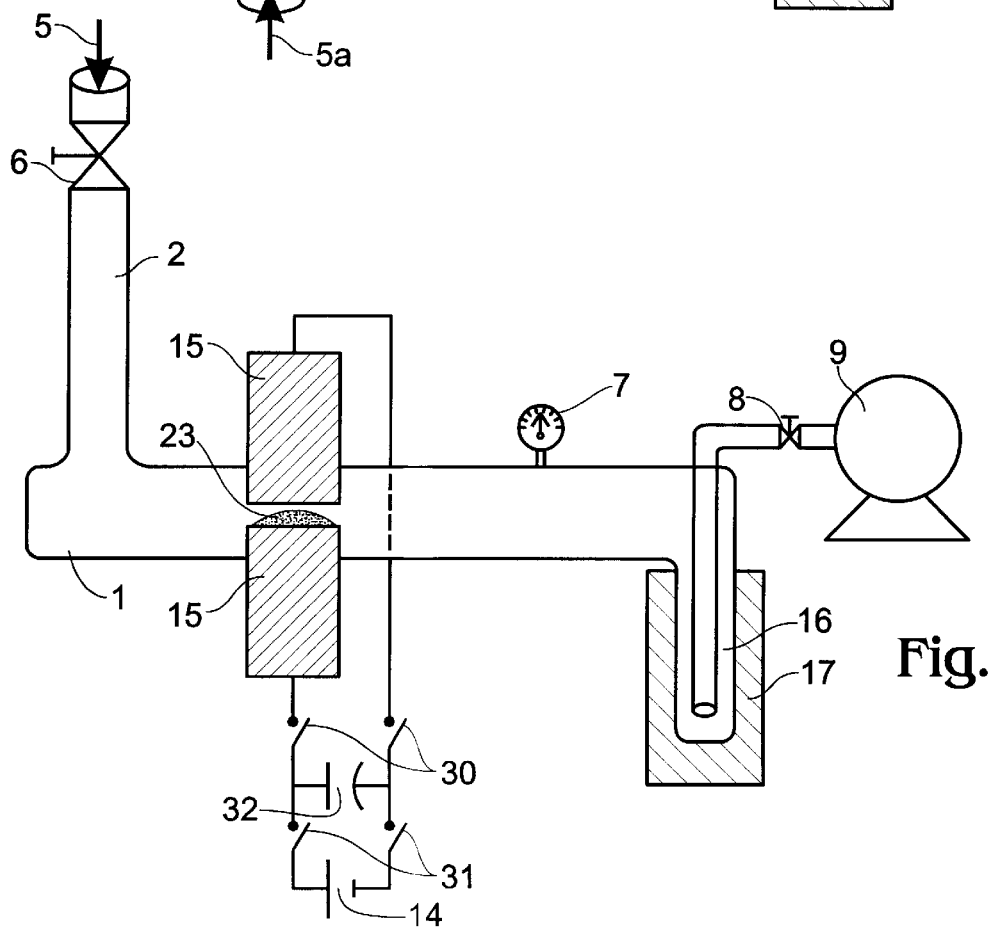

FIG. 8 is a schematic of still another exemplary reactor that is particularly designed to create a plasma to induce reaction of one or more low-volatility reactants. It comprises a pair of metal rods or plates 15 with smooth surfaces substantially parallel to each other and a relatively short distance (less than 1 mm) apart that serve as electrodes. One or more solid reactants 23 can be placed on the surface of the lower electrode. The remaining space between the electrodes can contain another gas-phase reactant or an inert gas such as argon, which enter through reactant inlet opening 5 and flow control valve 6. A plasma is generated and reaction initiated by a short-lived (0.001 to 1.0 second) DC discharge from one or more capacitors 32. The DC discharge is formed by first opening circuit switches 30 and closing switches 31 so that capacitor 32 is charged by DC voltage source 14. The short-lived DC discharge is then produced by opening switches 31 and closing switches 30. The plasma is generated by ionization of the gaseous materials or the volatilized reactants. During such a discharge, very high temperatures may be reached, causing rapid reaction of the low-volatility solid reactants, but the temperature rapidly returns to near ambient temperature, thereby preventing undesirable thermal decomposition of the products.

An important feature of the plasma synthesis processes and reactors described herein is that synthesis conditions have been shown to be sufficiently controlled that product mixtures can be reproduced. Thus, product mixtures produced under nominally ideal conditions at different times have been shown to contain substantially the same compounds in substantially the same relative amounts.

Many other reactor types are envisioned as being useful in carrying out the invention. For example, reactants can be excited by a variety of energy sources such as high intensity radiation with wavelengths in the visible or ultraviolet ranges. In such cases, the apparatus would be modified so that one or more of the reactants would be passed through an activation zone where high intensity radiation would interact with the reactants. This may be accomplished, for example, by passing a laser beam through the wall of the reactor at a point relatively transparent to the laser radiation. This light can interact with the reactants in much the same way as the high frequency voltage source to ionize or fragment a portion of the reactants to initiate reaction.

As to the screening aspect of the present invention, the basic process for screening plasmasynthesized mixtures for bioactivity comprises the steps:

(a) preparing the crude compound mixture for initial bioactivity screening tests;

(b) performing initial bioactivity screening tests on the crude compound mixture to determine if desired activity is present;

(c) if the desired activity is present, fractionating the crude compound mixture, testing each fraction for bioactivity, and refractionating and testing the active fractions until isolated compounds are found that show desired bioactivity; and (d) identifying the isolated compounds that show the desired bioactivity.

The crude product mixtures produced in the reactors described above can contain from near zero to 99% unreacted starting material and inert polymeric material, in addition to from 1 to 100 or more principal new products. However, typically the amount of unreacted starting material and inert polymeric is 50% to 99%. Bioactivity screening tests require as little as 100 nanograms or less of each new product, and so conversion of as little as 1% of the reactants to new products represents an acceptable yield. However, in many cases it is desirable to remove insoluble material, separate reactants that are present in large quantity from the new products, and to fractionate very large product mixtures into a number of mixtures that contain fewer compounds prior to bioactivity screening. A number of conventional laboratory procedures may be used to prepare and fractionate crude product mixtures prior to initial bioactivity screening tests. These include solvent extraction, dissolution, and simple filtration to remove objectionable polymeric and tar-like materials; high performance liquid chromatography (HPLC), column chromatography, size-exclusion chromatography, distillation, fractional crystallization, electrophoresis, and gas chromatography to fractionate very large product mixtures and to remove reactants that may be present in large excess. The crude product mixtures may also be evaluated for the yield and number of new products using these fractionation procedures in addition to gas chromatography/mass spectroscopy (GC/MS) and the relatively new technique of liquid chromatography/multistage mass spectroscopy (LC/MS").

There are a wide variety of conventional tests that have been developed to measure bioactivity. These tests are readily available and may be conducted using methods known to those skilled in the art, as described for example in Houghten, 13 *Biotech.* 412–421 (1992). In fact, the science and technology of bioactivity screening has progressed to the extent that companies exist, such as CEREP Inc., Celle I' Evescault, France, that can conduct a wide variety of specific bioactivity screening tests on customer's samples on a contract basis. In general, according to the invention, activity is screened by contacting the mixture of compounds with one of the following: a cell receptor, a cloned cell receptor, a biopolymer (protein, peptide, carbohydrate or nucleic acid), a model complexing agent for a bioreceptor or other biopolymer, an enzyme, a biological membrane or an organism.

The tests generally involve contacting a solution of the mixture of compounds to be tested with a bioreceptor, enzyme, or organism, and measuring enhancement or inhibition of binding to the bioreceptor, chemical activity of the enzyme, or activity of the organism. Useful activities include: binding, inhibition of binding, enzyme inhibition, enzyme enhancement inhibition of biopolymer interaction, enhancement of biopolymer interaction, translocation across a biological membrane, enhancement of genetic expression, inhibition of genetic expression, inhibition of growth or activity of an organism and enhancement of growth or activity of an organism.

For example, cell receptors, cloned cell receptors, or model complexing agents for bioreceptors may be complexed with a radio-labeled ligand. The bioreceptor complex is then added to a solution containing the mixture of test compounds and bioactivity is indicated by the appearance of uncomplexed radiolabeled ligand in the solution due to its displacement from the bioreceptor by a test compound. Tests using biologically important enzymes involve adding test compounds to a solution containing the enzyme and all of the reactants that are involved in the specific enzymatic reaction of interest. Bioactivity is indicated when addition of the test compounds produces an enhancement, or inhibition, of the enzymatic reaction as measured by the conversion rate of reactants to products. Tests using organisms involve adding the organism to a solution or culture broth containing test compounds and measuring the activity (growth or mortality) of the organism. For example, the organism could be bacteria for bioactivity tests for new potent antibiotics, or plant cells for bioactivity tests for development of new plant growth hormones.

High throughput screening (screening as many as 10,000 new compounds in one week) is accomplished by using robotic equipment to perform routine sample preparation and analysis tasks, and by performing individual tests on mixtures of 10 to 100 or more compounds at once. In this manner, a single negative test (i.e., no bioactivity found) can confirm that 100 or more test compounds do not show the desired bioactivity. Compound mixtures that do show the desired bioactivity are fractionated, for example, by using the methods noted above, and the fractions, sub-fractions, and finally, individual fractionated compounds are retested to determine which compound or compounds show the desired bioactivity.

Once the compound or compounds that exhibit the desired bioactivity are isolated, their specific identity and chemical structure is determined using conventional laboratory techniques that include elemental analysis, nuclear magnetic resonance (NMR) spectroscopy, infrared (IR) spectroscopy, and mass spectroscopy (MS).

EXAMPLE 1

Figure 9:
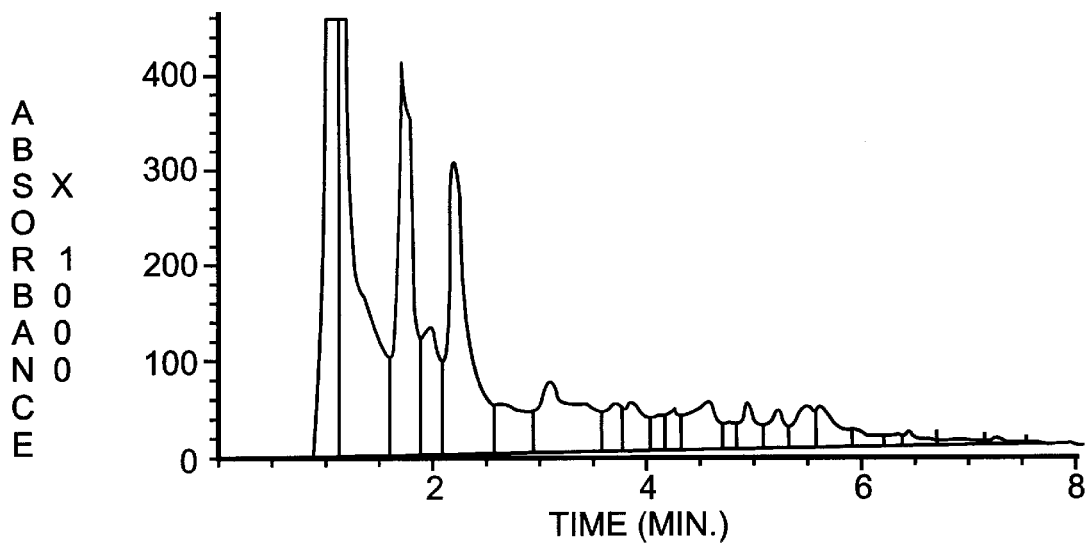
FIGS. 9, 11, 12, 15, 17, 19, 20, 22, and 23 are high-performance liquid chromatography (HPLC) plots of absorbance versus time of organic compound mixtures prepared as described in Examples 1–9.
Figure 10:
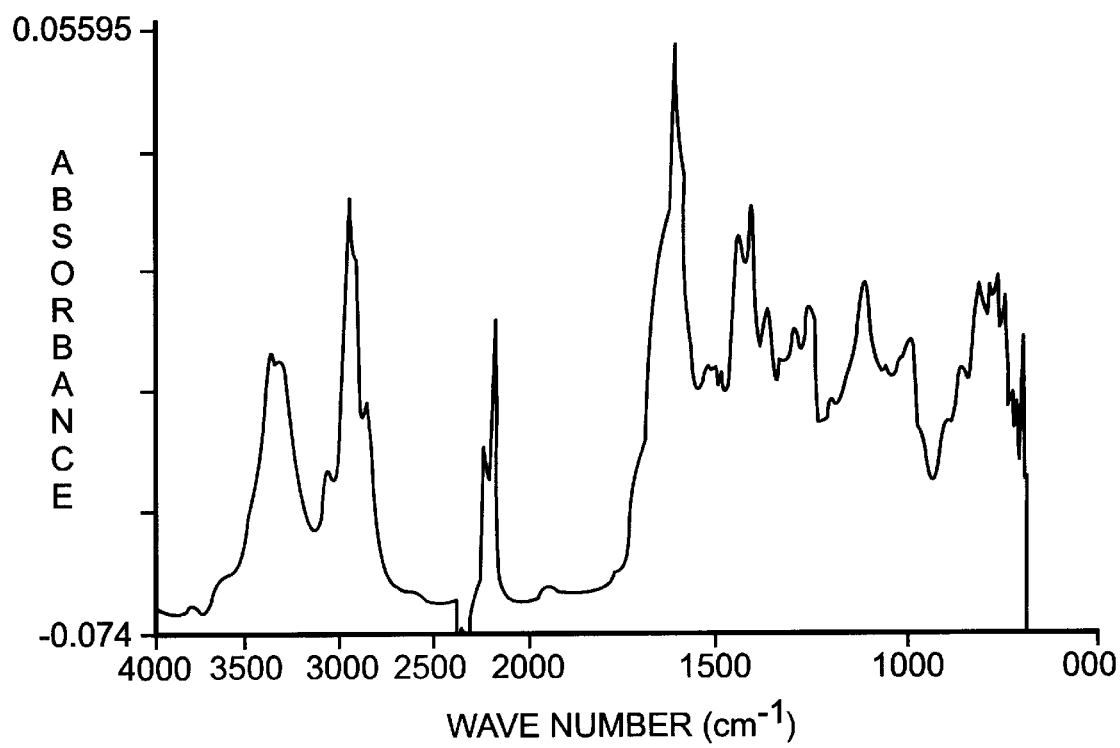
FIGS. 10, 13, 16, and 18 are infrared spectra of organic compound mixtures prepared as described in Examples 1 and 3–5.

A product mixture containing at least 20 new compounds suitable for bioactivity screening tests was synthesized using the plasma synthesis reactor shown in FIG. 4. Acetylene gas, water vapor, and ammonia gas were introduced to the reactor through reactant inlet opening 5b at 50, 180, and 340 $cm^3$ (STP)/min, respectively. The pressure was adjusted to 3.0 torr and 150 watts of plasma discharge power at 50 kHz was applied to 4.4 cm-diameter tubular internal electrodes that were spaced 21 cm apart, and cooled by the circulation of cold water through the annulus of the tubular electrodes. After 2 hours reaction time a red-brown oily product mixture was recovered from cold trap 16 in a 9.2% yield based on the quantity of acetylene fed into the reactor. The HPLC chromatogram, using UV detection at 230 nm, of the product mixture is shown in FIG. 9. By virtue of its absorption peaks, this chromatogram demonstrates that the product mixture contained at least 20 new compounds. The infrared spectrum of the product mixture is shown in FIG. 10, which reveals that the new compounds in the product mixture contained hydroxyl, amine, amide, methyl, methylene, terminal and branched alkyne and allene functional groups. This Example demonstrates the direct conversion of gas and vapor reactants to a multiplicity of new products by passing all reactants through a plasma formed from the reactants themselves that is sustained by internal electrodes.

EXAMPLE 2

Figure 11:
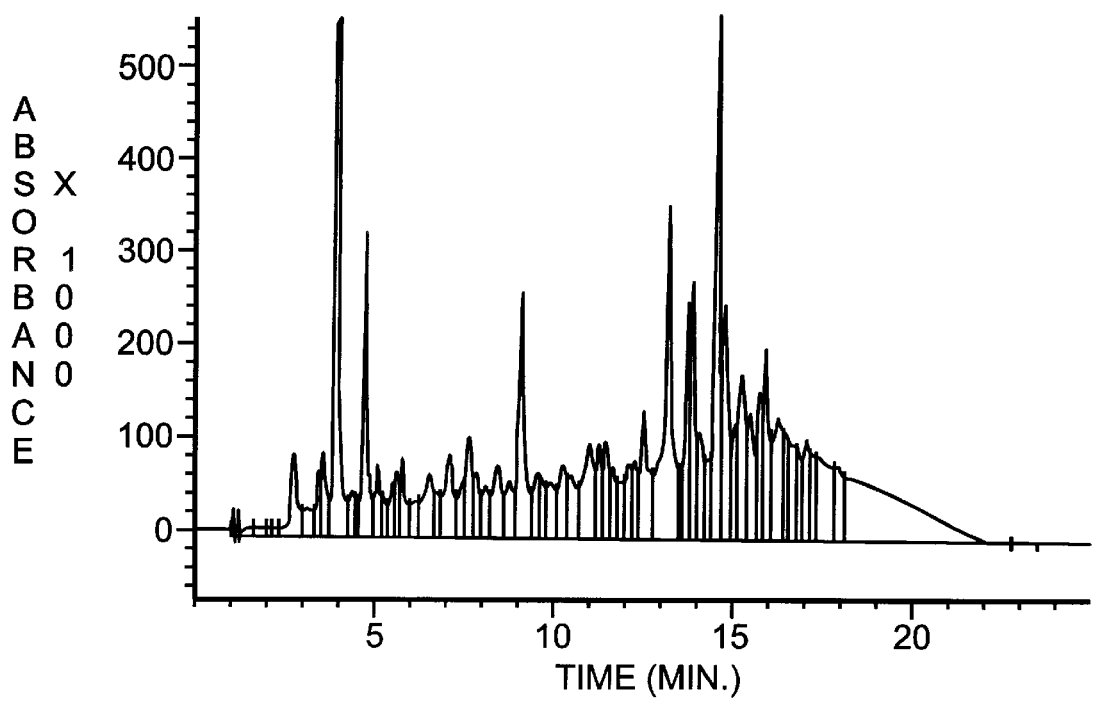

A product mixture containing at least 35 new compounds suitable for bioactivity screening was synthesized using the plasma synthesis reactor shown in FIG. 4. Cyclopentanone and allylamine vapors were introduced to the reactor through reactant inlet opening 5b at 100 and 30 $cm^3$ (STP)/min, respectively. Pressure was adjusted to 1.0 torr and 200 watts of plasma discharge power at 50 kHz was applied to 4.4 cm-diameter tubular, water-cooled internal electrodes spaced 20 cm apart. After 35 minutes reaction time a dark brown liquid product mixture was recovered from cold trap 16 in a 4% yield based on the quantity of reactants fed into the reactor. The HPLC chromatogram, using UV detection at 214 nm, of the product mixture is shown in FIG. 11. This chromatogram demonstrates that the product mixture contained at least 35 new compounds. This Example serves as a comparison to Example 3 and demonstrates the direct conversion of vapor reactants to new products by passing all reactants through a plasma that is sustained by internal electrodes.

EXAMPLE 3

Figure 12:
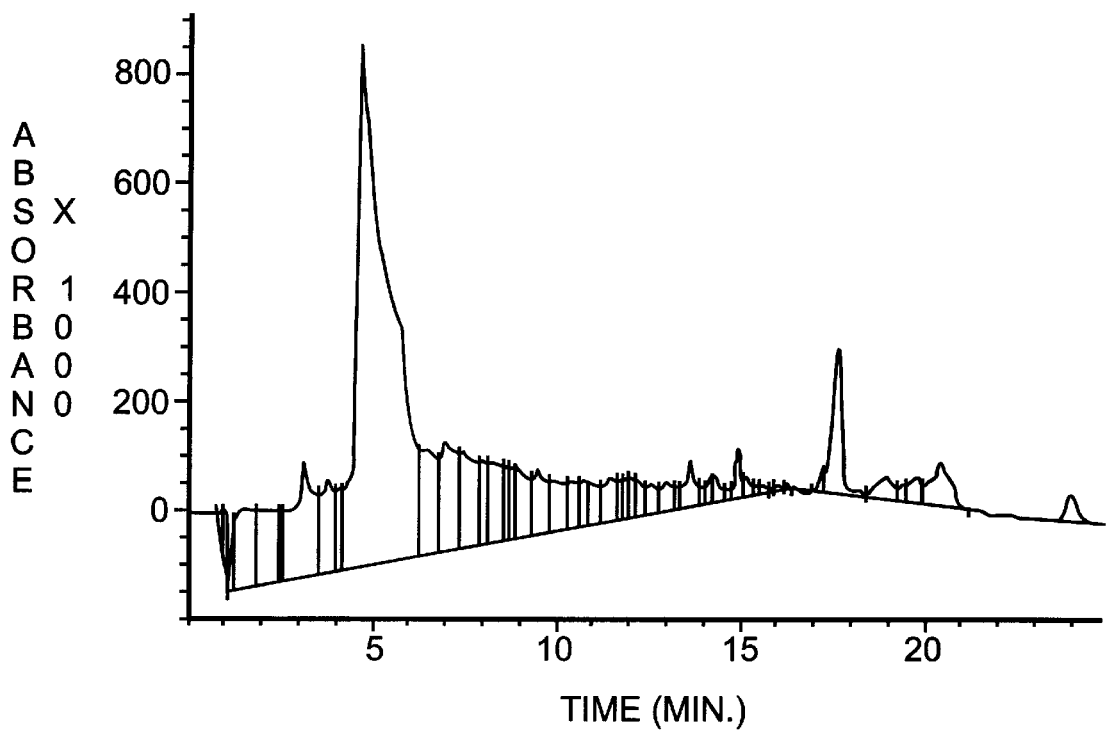
Figure 13:
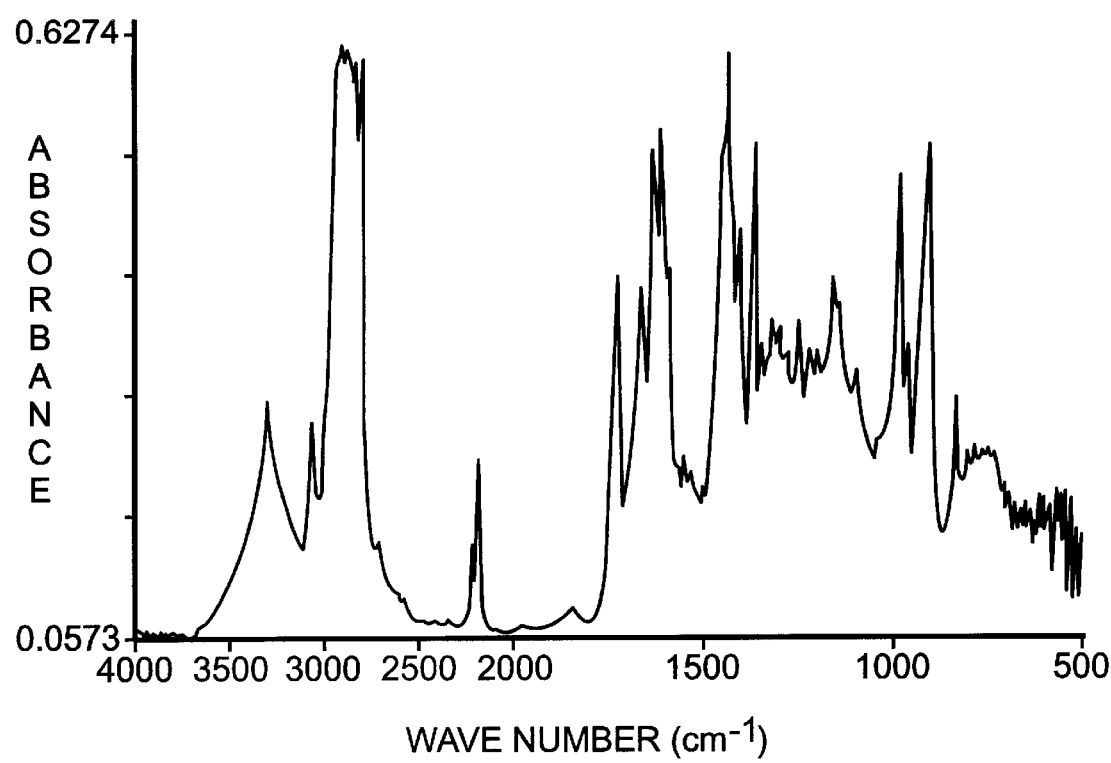
Figure 14A:
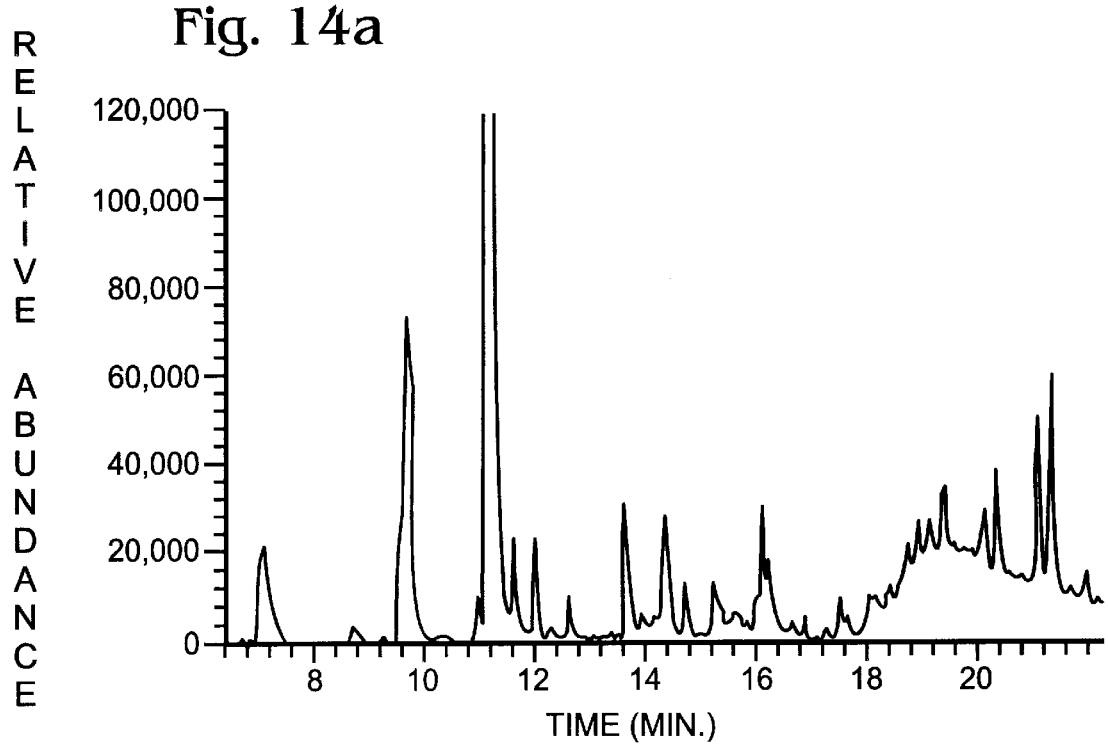
FIG. 14a and 14b are gas chromatography/mass spectroscopy chromatogram of the organic compound mixture prepared as described in Example 3.
Figure 14B:
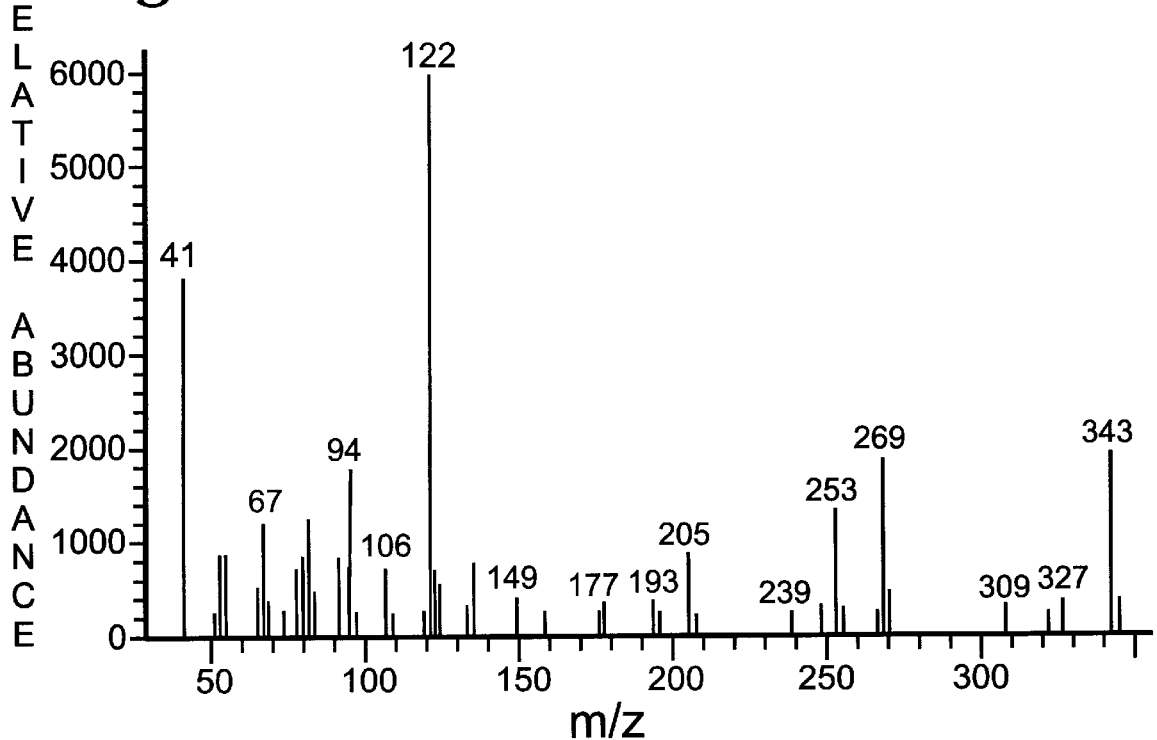

Example 2 was substantially repeated except cyclopentanone and allylamine vapors were introduced to the reactor through reactant inlet opening 5c, argon gas was introduced to the reactor through reactant inlet opening 5b at 50 $cm^3$ (STP)/min, the pressure was 2.0 torr, and the reaction time was 1.5 hours. A transparent red oily liquid product was recovered from cold trap 16 in a 26% yield based on the quantity of reactants fed into the reactor. The HPLC chromatogram, using UV detection at 214 nm, of the product mixture is shown in FIG. 12. This chromatogram demonstrates that the product mixture contained at least 30 new compounds that are distinct from the compounds produced in Example 2. The IR spectrum of the product mixture, after distillation to remove unreacted cyclohexanone and allylamine, is shown in FIG. 13. This spectrum shows that the new compounds in the product mixture contained amine, olefin, methyl, methylene, aldehyde, alkyne, allene, ester, and ketone functional groups. The results of GC/MS analysis of the product mixture, after distillation, is shown in FIGS. 14a and 14b. FIG. 14a shows the GC chromatogram of the sample and demonstrates the resolution of at least 28 new compounds. FIG. 14b shows the mass spectrum of compounds eluting the gas chromatograph at 21.16 minutes. The indicated mass of the molecular ion, or highest mass fragment was 343 daltons. The molecular weight of cylopentanone and allylamine are 84 and 57 daltons, respectively. Thus, the mass spectrum confirms the production of products that are substantially distinct from the reactants. This Example also demonstrates the indirect conversion of vapor reactants to new products by reaction downstream of the plasma zone, with inert gas excited-state species.

EXAMPLE 4

Figure 15:
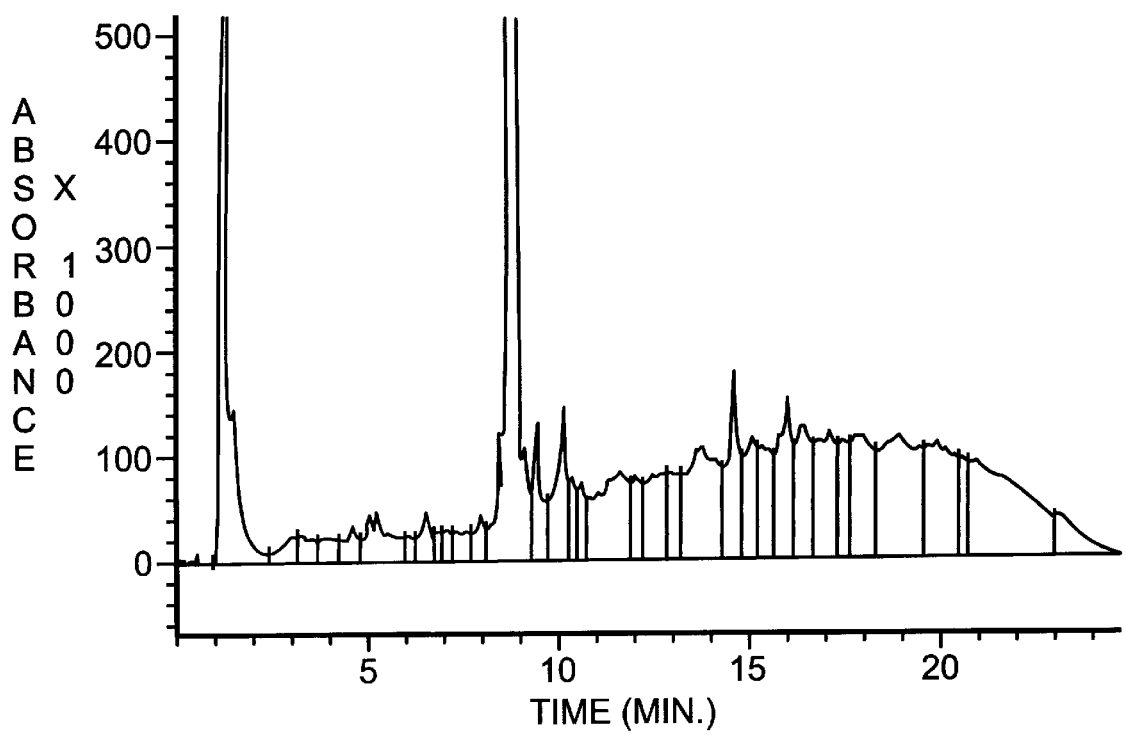
Figure 16:
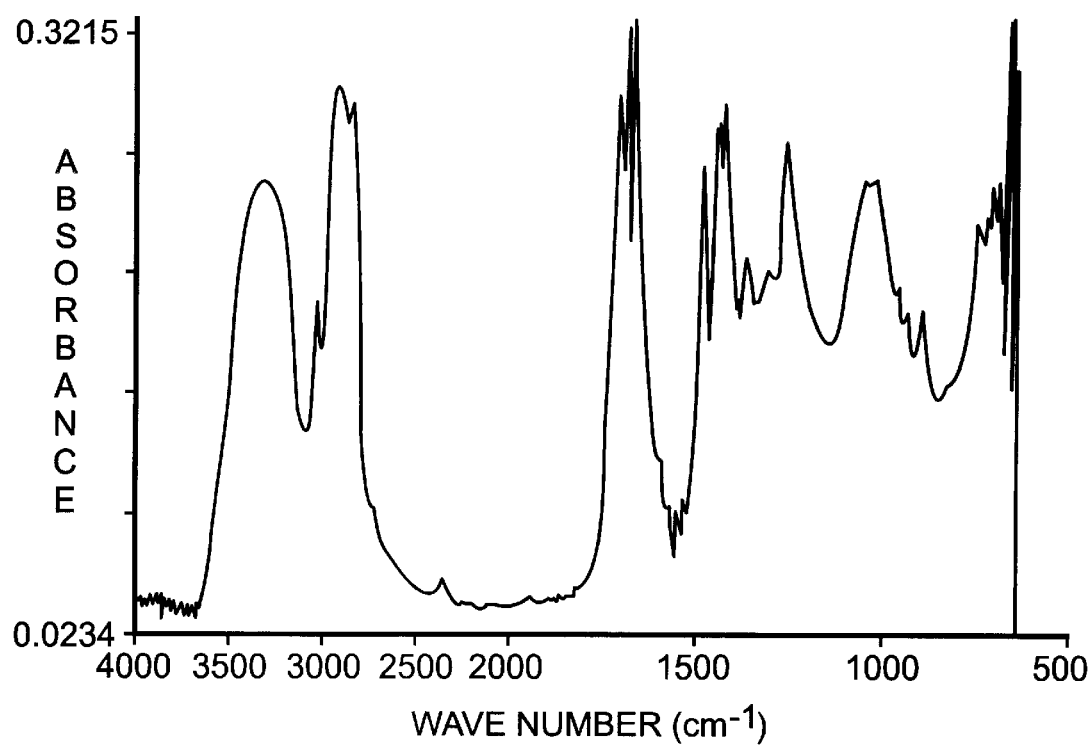

A product mixture containing at least 29 new compounds suitable for bioactivity screening was synthesized using the plasma synthesis reactor shown in FIG. 3. 5-Norbornene-2-methanol (10 g) and 2-imidazolidone (10 g) were added to vacuum flask 1. The pressure was adjusted to 1.0 torr and heating mantle 12 was set so that the flask temperature was maintained at approximately 80° C., whereupon the reactants formed a gently refluxing viscous amber solution. A plasma was formed near the bottom of condenser 3 within the reflux zone of the reactants by applying 50 watts of plasma discharge power at 13.56 MHz to 3.5 cm diameter external electrodes spaced 12 cm apart. After 8 hours' reaction time the flask contained approximately 20 g of a dark amber semi-solid. The HPLC chromatogram, using UV detection at 214 nm, of the product mixture is shown in FIG. 15. This chromatogram demonstrates that the crude product mixture contains at least 29 new compounds. The crude product mixture was then dissolved in diethylether and extracted with water to remove unreacted 2-imidazolidone. The ether phase was then distilled at ambient pressure to remove the diethylether, then at hard vacuum and 75° C. to remove unreacted 5-norbornene-2-methanol, to produce an amber resinous product which was confirmed by HPLC analysis to be free of the initial reactants. The infrared spectrum of the purified product mixture is shown in FIG. 16. This spectrum shows that the new compounds in the product mixture contained hydroxyl, olefin, methyl, methylene, carbonyl, and amine functional groups. This Example demonstrates the direct conversion of low-volatility liquid and low-melting solid reactants to new products by refluxing all the reactants within a plasma that is sustained by external electrodes.

EXAMPLE 5

Figure 17:
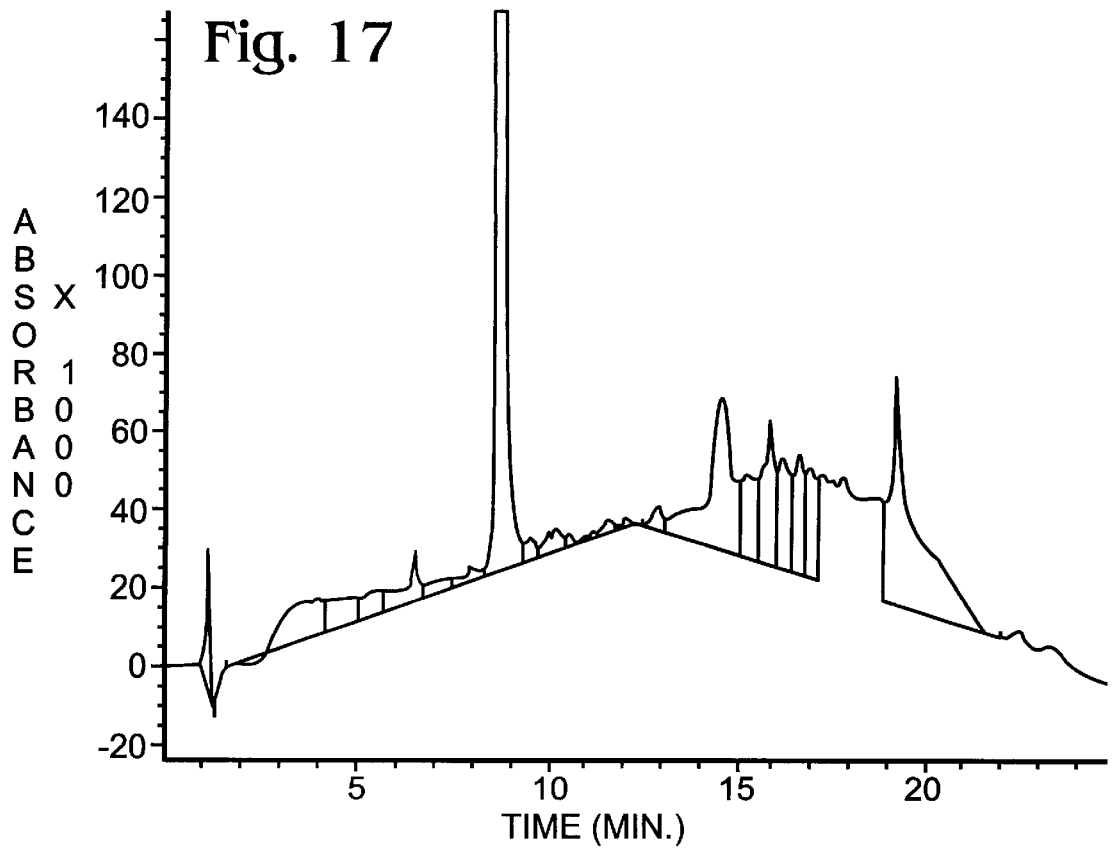
Figure 18:
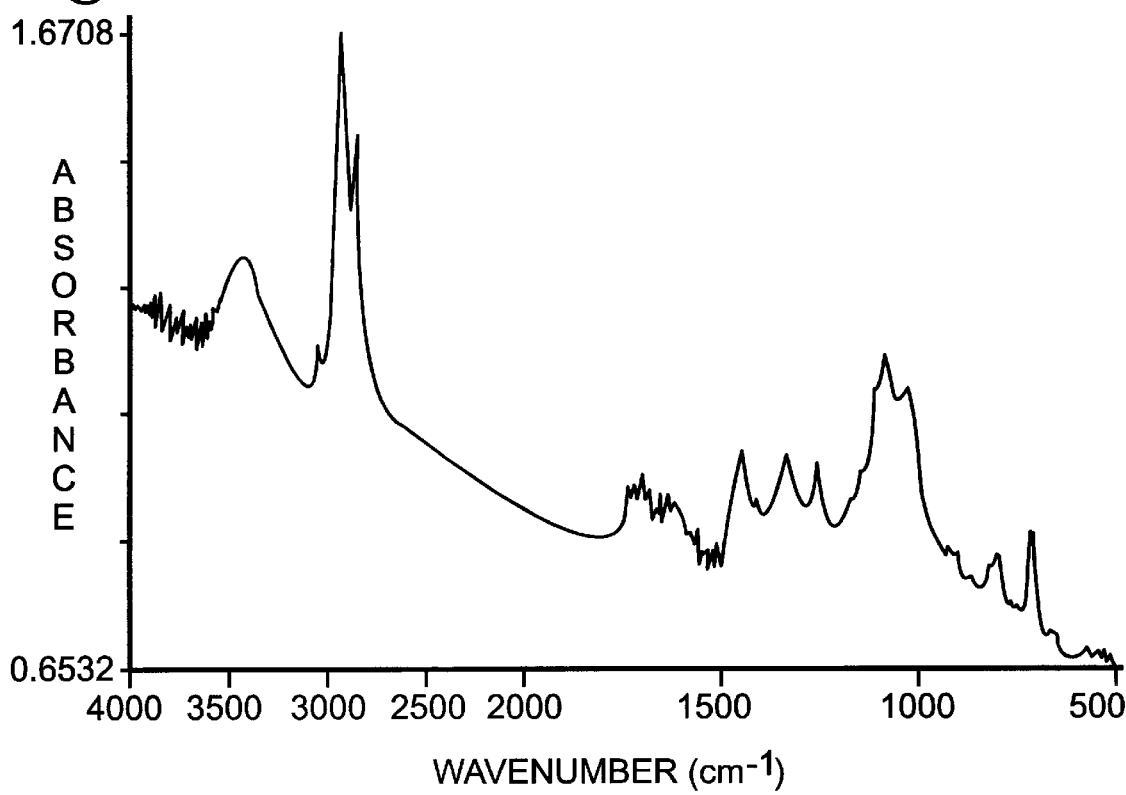

A product mixture containing at least 20 new compounds suitable for bioactivity screening was synthesized using the plasma synthesis reactor shown in FIG. 1. 5 Norbornene-2-methanol (15 g) was added to vacuum flask 1 and difluoromethane gas was introduced into the reactor through reactant inlet opening 5 at 400 cm$^3$ (STP)/min. The pressure was adjusted to 1.0 torr and heating mantle 12 was set so that the flask temperature was maintained at approximately 80° C., whereupon the 5-norbornene-2-methanol reactant formed a gently refluxing viscous amber solution. A plasma was formed within reactant inlet 2 by applying 100 watts of plasma discharge power at 13.56 MHz to 3.5 cm diameter external electrodes that were spaced 8 cm apart. After 1.5 hours reaction time the flask contained approximately 15 g of a dark semi-solid. The HPLC chromatogram, using UV detection at 214 nm, of the product mixture is shown in FIG. 17. This chromatogram demonstrates that the crude product mixture contained at least 20 new compounds. Unreacted 5-norbornene-2-methanol was removed from the crude product mixture by distillation at hard vacuum and 75° C. to produce a dark solid resinous product. The IR spectrum of the purified product mixture is shown in FIG. 18. This spectrum shows that the new compounds in the product mixture contained hydroxyl, olefin, methyl, methylene, carbonyl, and fluoro functional groups. This Example demonstrates the conversion of a low volatility liquid reactant to new products by contacting the refluxing vapor with excited-state species produced by passing a reactive gaseous reactant through a plasma zone that is sustained by external electrodes.

EXAMPLE 6

Figure 19:
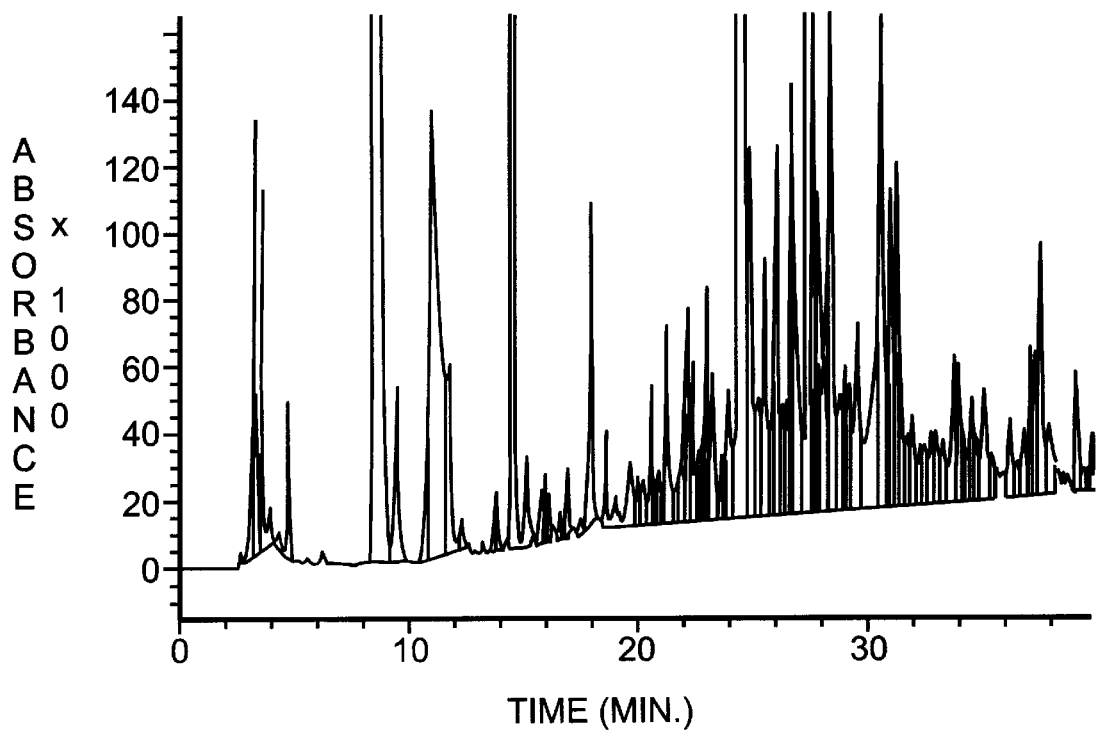

A product mixture containing at least 120 new compounds suitable for bioactivity screening was synthesized using the plasma synthesis reactor shown in FIG. 3. Resorcinol (5 g) and 1,2,3,4-tetrahydro-1-napthylamine (5 g) were added to vacuum flask 1. Hexanes (a commercial mixture of hexane isomers) vapor was then introduced into the reactor through reactant inlet opening 5 at 5.5 cm$^3$ (STP)/min. Pressure was adjusted to 0.15 torr and heating mantle 12 was set so that the flask temperature was maintained at approximately 120° C., whereupon the reactants formed a gently refluxing amber solution. A plasma was formed near the bottom of condenser 3 within the reflux zone of the reactants by applying 140 watts of plasma discharge power at 13.56 MHz to 3.5 cm diameter external electrodes spaced 4 cm apart. After 2.75 hours reaction time, 6.5 g of a glassy red-brown solid product mixture was recovered from flask 1. A sample of the crude product mixture was dissolved in a solution of 50% acetonitrile in water, filtered to remove insoluble matter, and analyzed by HPLC. The HPLC chromatogram, using UV detection at 254 nm, of the filtered product mixture is shown in FIG. 19. This chromatogram demonstrates that the crude product mixture contained at least 120 new compounds. The filtered product mixture was then fractionated by HPLC to remove unreacted resorcinol and 1,2,3,4-tetrahydro-1-napthylamine. The fractions containing the new product compounds were pooled and tested for bioactivity in receptor competitive-binding tests. At least one compound in this product mixture was found to be active for binding to the cannabis CB-1 receptor, and to the opioid K-type receptor. This Example demonstrates the direct conversion of two low-volatility liquid reactants and one high-volatility liquid reactant, to new products that are bioactive, by refluxing all reactants within a plasma that is sustained by external electrodes.

EXAMPLE 7

Figure 20:
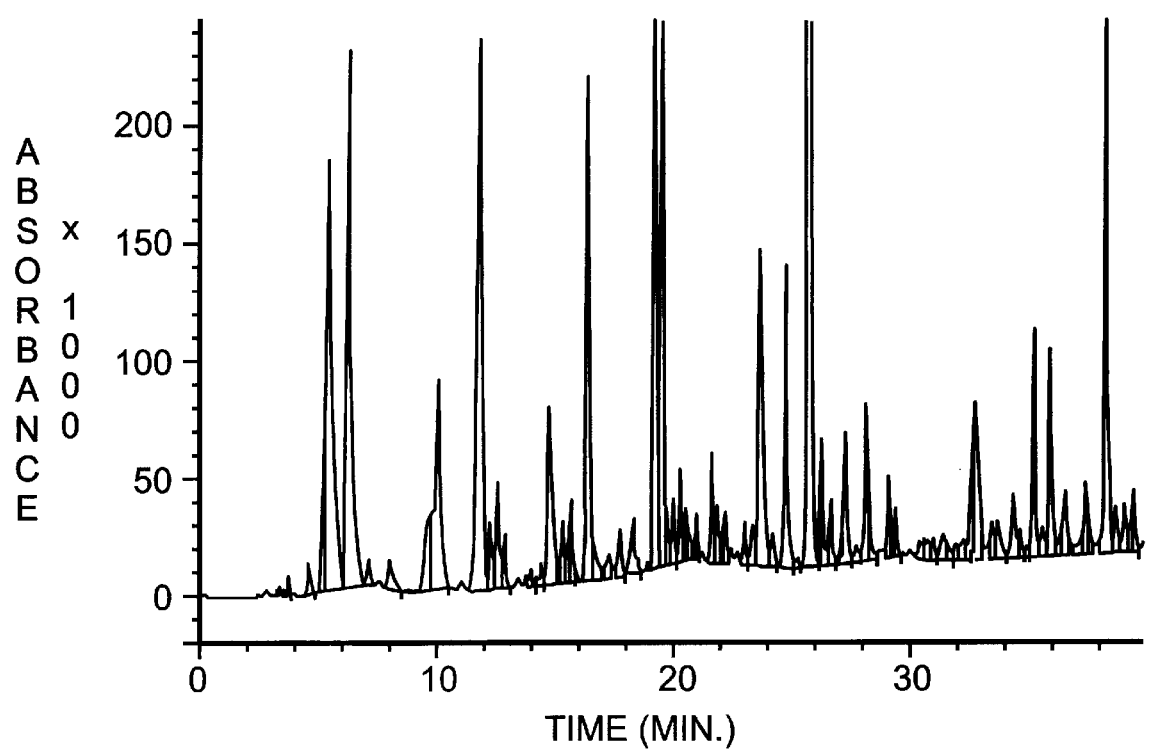
Figure 21:
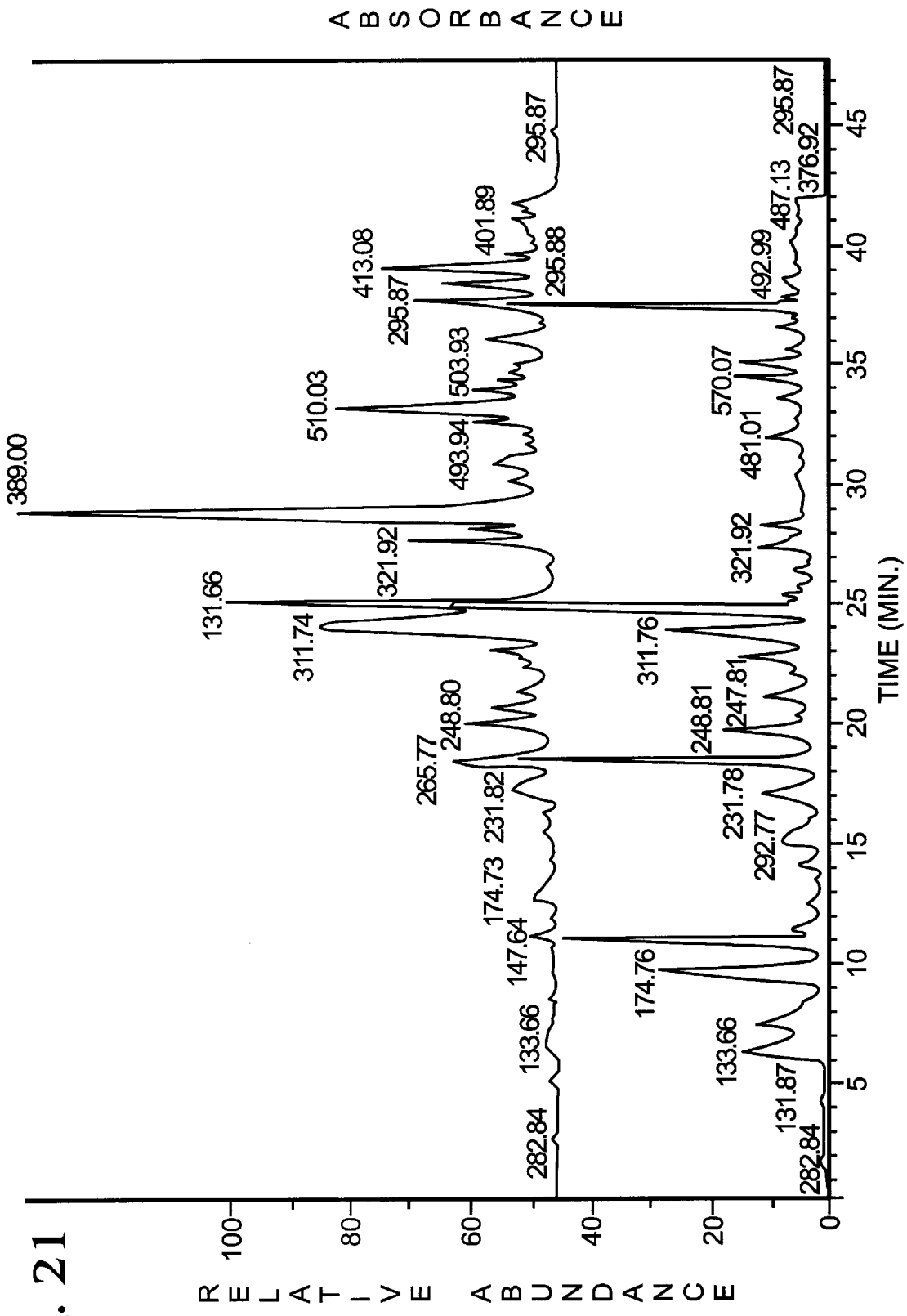
FIG. 21 is a HPLC/mass spectroscopy chromatogram of the organic compound mixture produced in Example 7.

Example 6 was substantially repeated except that 1,2,3,4-tetrahydroisoquinoline (5.0 g) and olivetol (4.5 g) were added to vacuum flask 1, the pressure was 0.50 torr, and the reaction time was 4 hours. The resulting synthesis left 8.8 g of a dark amber-brown semi-solid product. A sample of the crude product mixture was dissolved in a solution of 50% acetonitrile in water, filtered to remove insoluble matter, and analyzed by HPLC. The HPLC chromatogram, using UV detection at 254 nm, of the filtered product mixture is shown in FIG. 20. This chromatogram demonstrates that the crude product mixture contained at least 129 new compounds. An HPLC/MSn chromatogram of the filtered product mixture is shown in FIG. 21. This chromatogram confirms the production of new compounds with molecular weights that range from 132 daltons to 570 daltons. The filtered product mixture was then fractionated by HPLC to remove unreacted 1,2,3,4-tetrahydroisoquinoline and olivetol. The fractions containing the new product compounds were pooled and tested for bioactivity in receptor binding tests. At least one compound in this product mixture was found to be active for binding to the cannabis CB-1 receptor, and to the opioid K-type receptor.

EXAMPLE 8

Figure 22:
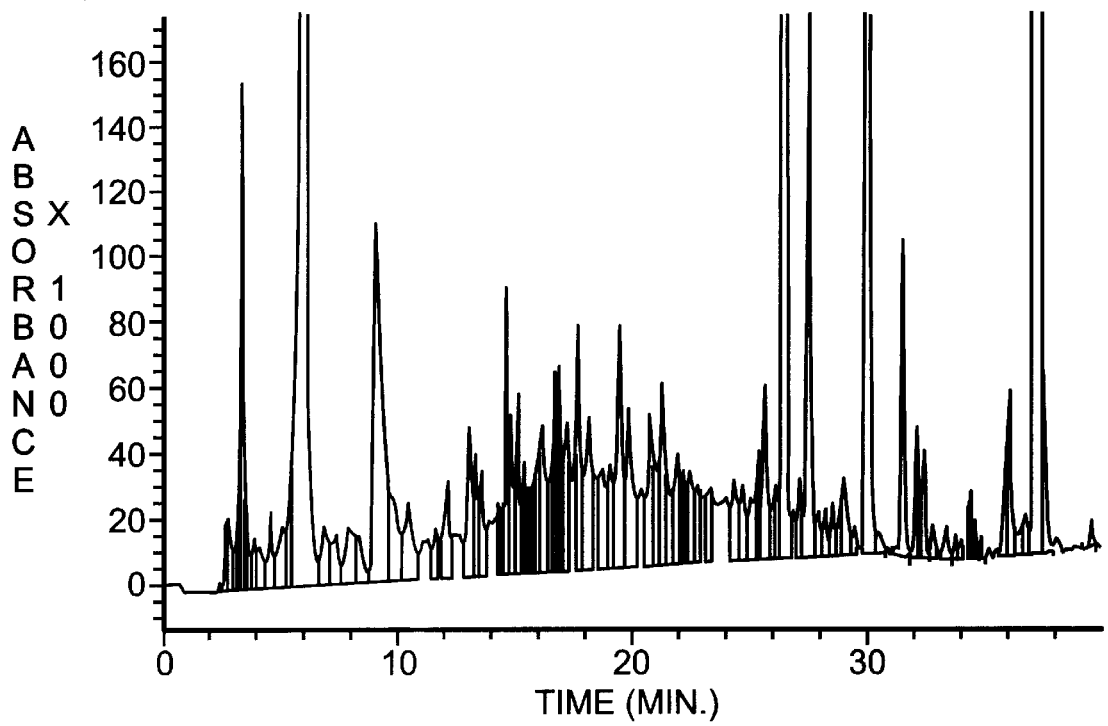

Example 6 was substantially repeated except that 9-vinylcarbazole (5.0 g) and 3,4-dimethoxyphen-ethylamine (5.0 g) were added to vacuum flask 1, argon was introduced into the reactor through reactant inlet opening 5 at 10.8 cm$^3$ (STP)/min, the pressure was 1.0 torr, the power was 100 watts, and the reaction time was 4 hours. The resulting synthesis left 7.4 g of a viscous transparent red solution that formed a red semi-solid product upon cooling. A sample of the crude product mixture was dissolved in a solution of 50% acetonitrile in water, filtered to remove insoluble matter, and analyzed by HPLC. The HPLC chromatogram, using UV detection at 254 nm, of the filtered product mixture is shown in FIG. 22. This chromatogram demonstrates that the crude product mixture contained at least 126 new compounds. The filtered product mixture was then fractionated by HPLC to remove unreacted 9-vinylcarbazole and 3,4-dimethoxyphenethylamine. The fractions containing the new product compounds were pooled and tested for bioactivity in receptor binding tests. At least one compound in this product mixture was found to be active for binding to the opioid K-type receptor.

EXAMPLE 9

Figure 23:
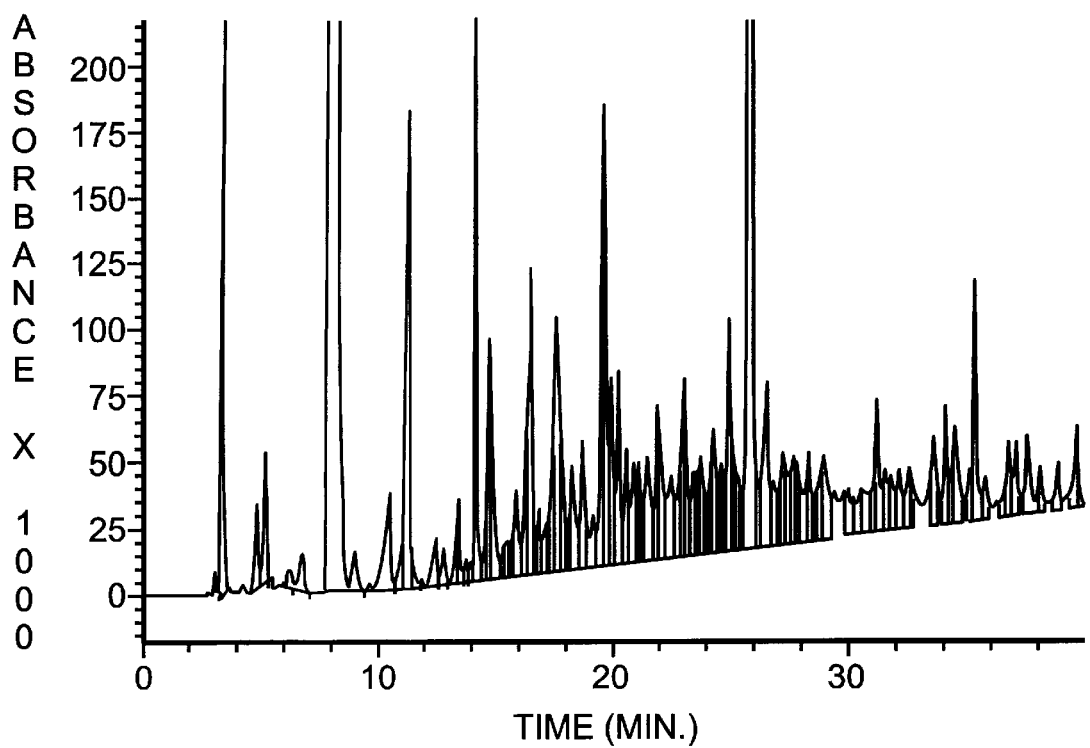

Example 6 was substantially repeated except resorcinol (5.0 g) and olivetol (4.5 g) were added to vacuum flask 1, the pressure was 1.0 torr, the power was 250 watts, and the reaction time was 4 hours. The resulting synthesis left 8.8 g of a dark red-brown oily liquid product. A sample of the crude product mixture was dissolved in a solution of 50% acetonitrile in water, filtered to remove insoluble matter, and analyzed by HPLC. The HPLC chromatogram, using UV detection at 254 nm, of the filtered product mixture is shown in FIG. 23. This chromatogram demonstrates that the crude product mixture contained at least 127 new compounds. The filtered product mixture was then fractionated by HPLC to remove unreacted resorcinol and olivetol. The fractions containing the new product compounds were pooled and tested for bioactivity in receptor binding tests. A compound, or compounds in this product mixture was found to be active for binding to the opioid K-type receptor.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A method for forming and assaying organic compounds for bioactivity comprising the steps:
   (a) providing a starting material comprising at least one organic compound;
   (b) subjecting said starting material to a plasma to form a product mixture of organic compounds containing at least one organic compound that is not said starting material; and
   (c) subjecting said product mixture to an assay for bioactivity.

2. The method of claim 1 wherein said product mixture contains at least five organic compounds that are not said starting material.

3. The method of claim 1 wherein said assay for bioactivity comprises:
   (a) contacting said product mixture with an agent selected from the group consisting of a cell receptor; a cloned cell receptor; a biopolymer selected from the group consisting of a protein, a peptide, a carbohydrate and a nucleic acid; a model complexing agent for a bioreceptor; an enzyme; a biological membrane; and an organism; and
   (b) determining whether any compound in said product mixture exhibits an activity selected from the group of activities consisting of binding, inhibition of binding, enzyme inhibition, enzyme enhancement, inhibition of biopolymer interaction, enhancement of biopolymer interaction, translocation across a biological membrane, inhibition of translocation across a biological membrane, enhancement of genetic expression, inhibition of genetic expression, inhibition of the growth or activity of an organism, and enhancement of the growth or activity of an organism.

4. The method of claim 1 wherein, prior to step (c), said product mixture is further separated into fractions containing at least one compound.

5. The method of claim 1 wherein said starting material includes at least one organic compound that is a bioactive compound.

6. The method of claim 1 wherein said plasma of step (b) is generated by a continuous electric field to form said plasma.

7. The method of claim 6 wherein said electric field is selected from direct current and alternating current.

8. The method of claim 7 wherein the residence time of said starting material in said plasma zone is from 0.001 to 10 seconds, the pressure of said plasma zone is from 0.05 to 10 torr, and the discharge power density of said plasma zone is from 10 to 5000 watts per liter of plasma zone volume.

9. The method of claim 7 wherein the residence time of said starting material in said plasma zone is from 0.01 to 2 seconds, the pressure of said plasma zone is from 0.1 torr to 3 torr and the discharge power density of said plasma zone is from 50 to 500 watts per liter of plasma zone volume.

10. The method of claim 7 wherein said starting material reacts with plasma-activated species outside of said plasma zone.

11. The method of claim 10 wherein the pressure and discharge power density of said plasma zone is from 0.05 torr to 10 torr and from 10 to 5000 watts per liter of plasma zone volume, respectively.

12. The method of claim 10 wherein the pressure and discharge power density of said plasma zone is from 0.1 torr to 3 torr and from 50 to 500 watts per liter of plasma zone volume, respectively.

13. The method of claim 1 wherein said plasma of step (b) is generated by a light source having a frequency range from microwave to X-ray.

14. The method of claim 13 wherein said light source emits radiation in the frequency range of from $10^{10}$ Hz to $10^{22}$ Hz.

15. The method of claim 13 wherein said light source is a laser.

16. The method of claim 13 wherein said light source is an electric discharge lamp.

17. The method of claim 1 wherein said plasma of step (b) is generated by an electron beam.

18. The method of claim 1 wherein said plasma of step (b) is generated by an alpha-particle beam.

* * * * *

UNITED STATES PATENT AND TRADEMARK OFFICE
CERTIFICATE OF CORRECTION

PATENT NO. : 5,772,855
DATED : June 30, 1999
INVENTOR(S) : Johnson, Babcock, West and Friesen It is certified that error appears in the above-identified patent and that said Letters Patent is hereby corrected as shown below:

Column 12,
Line 3, change "5*b*at" to read "5*b* at".

Signed and Sealed this

Twenty-third Day of October, 2001

Attest:

NICHOLAS P. GODICI
Attesting Officer   Acting Director of the United States Patent and Trademark Office